United States Patent
Harrison et al.

[11] Patent Number: 5,922,752
[45] Date of Patent: Jul. 13, 1999

[54] NMDA (N-METHYL-D-ASPARTATE) ANTAGONISTS

[75] Inventors: Boyd L. Harrison, Princeton Jct., N.J.; Raymond S. Gross, Mason; Bruce M. Baron, Cincinnati, both of Ohio

[73] Assignee: Hoechst Marion Roussell, Inc., Bridgewater, N.J.

[21] Appl. No.: 08/941,747

[22] Filed: Sep. 30, 1997

Related U.S. Application Data

[60] Provisional application No. 60/057,589, Jun. 11, 1997.

[51] Int. Cl.$^6$ ...................... A61K 31/405; C07D 209/12
[52] U.S. Cl. ............................................ 514/419; 548/491

[56] References Cited

U.S. PATENT DOCUMENTS

| | | | |
|---|---|---|---|
| 5,106,847 | 4/1992 | Salituro et al. | 514/232.5 |
| 5,519,048 | 5/1996 | Salituro et al. | 514/419 |
| 5,563,157 | 10/1996 | Harrison et al. | 514/339 |

FOREIGN PATENT DOCUMENTS

| | | |
|---|---|---|
| 0568136 | 11/1993 | European Pat. Off. . |
| 2266091 | 10/1993 | United Kingdom . |
| 9216205 | 10/1992 | WIPO . |
| 9321153 | 4/1993 | WIPO . |

OTHER PUBLICATIONS

Salitouro F.G. et al., Bioorganic & Medicinal Chem. Ltrs., vol. 1, No. 9, pp. 455–460, 1991.
Kemp John A., TiPS –Jan. 1993, vol. 14, No. 1, pp. 20–25.
Schelkun, R.M. et al, *33rd Nat's Organic Chemistry Symposium Bozeman, MT*–Jun. 1993 Abstract, #b–73.
Thornber, Chemical Society Review, vol. 8, No. 4, 1979.

*Primary Examiner*—Joseph K. McKane
*Attorney, Agent, or Firm*—Michael W. Ferrell; David M. Stemerick

[57] ABSTRACT

The present invention is new excitatory amino acid antagonists (herein referred to as compounds of formula (1)): below:

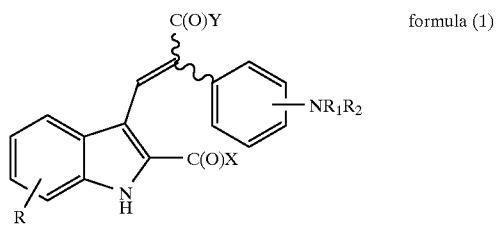

These new antagonists are useful as NMDA (N-methyl-D-aspartate) antagonists.

32 Claims, No Drawings

NMDA (N-METHYL-D-ASPARTATE) ANTAGONISTS

This application claims the benefit of U.S. Provisional Application Ser. No. 60/057,589, filed Jun. 11, 1997.

The present invention is directed to novel excitatory amino acid antagonists (herein referred to as compounds of formula (1)). These new antagonists are useful as NMDA (N-methyl-D-aspartate) antagonists and preferentially bind to the strychnine-insensitive glycine binding site on the NMDA receptor complex associated with the treatment of a number of disease states. Another aspect of the invention is directed to the use of compounds of formula (1) in the treatment of a number of diseases as well as to pharmaceutical compositions containing these excitatory amino acid antagonists.

SUMMARY OF THE INVENTION

In accordance with the present invention, a new class of NMDA antagonists have been discovered which is described by formula (1):

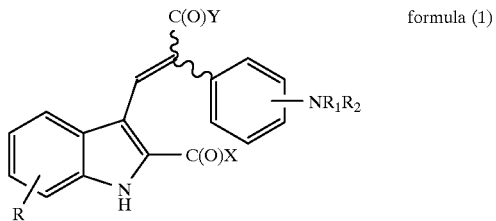

formula (1)

wherein

X is chosen from the group consisting of hydroxy, physiologically acceptable ester, and physiologically acceptable amide;

Y is chosen from the group consisting of hydroxy, physiologically acceptable ester, and physiologically acceptable amide;

R is from 1 to 3 substituents independently chosen from the group consisting of hydrogen, $C_1$–$C_4$ alkyl, $C_1$–$C_4$ alkoxy, halogen, —$CF_3$, and —$OCF_3$;

$R_1$ is chosen from the group consisting of hydrogen and $C_1$–$C_4$ alkyl;

$R_2$ is a radical chosen from the group consisting of

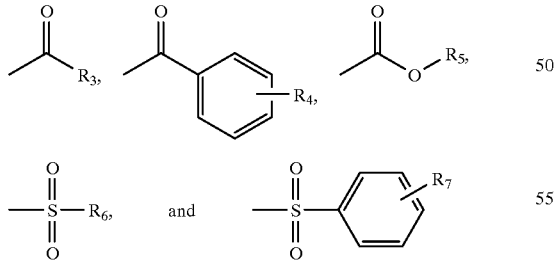

wherein $R_3$ is chosen from the group consisting of hydrogen and $C_1$–$C_4$ alkyl;

$R_4$ is from 1 to 2 substituents independently chosen from the group consisting of hydrogen, $C_1$–$C_4$ alkyl, $C_1$–$C_4$ alkoxy, halogen, and —$CF_3$;

$R_5$ is $C_1$–$C_4$ alkyl;

$R_6$ is $C_1$–$C_4$ alkyl;

$R_7$ is from 1 to 2 substituents independently chosen from the group consisting of hydrogen, $C_1$–$C_4$ alkyl, $C_1$–$C_4$ alkoxy, halogen, and —$CF_3$;

and pharmaceutically acceptable addition salts thereof.

As used in this application:

a) the term "$C_1$–$C_4$ alkyl" refers to a branched or straight chained alkyl radical containing from 1–4 carbon atoms, such as methyl, ethyl, n-propyl, isopropyl, n-butyl, secbutyl, isobutyl, t-butyl, and the like;

b) the term "$C_1$–$C_4$ alkoxy" refers to a branched or straight chained alkoxy radical containing from 1–4 carbon atoms, such as methoxy, ethoxy, n-propoxy, isopropoxy, n-butoxy, secbutoxy, isobutoxy, t-butoxy, and the like;

c) the term "halogen" refers to a fluorine atom, a chlorine atom, a bromine atom, or a iodine atom;

d) the term "physiologically acceptable ester" refers to any non-toxic ester or any prodrug that allows the compounds of this application to function as NMDA antagonist: these physiologically acceptable esters may be chosen from but are not limited to compounds wherein X and Y may each independently be represented by —$OR_8$, —$OCH_2OR_8$ or —O—$(CH_2)_p$—$NR_9R_{10}$; in which $R_8$ is represented by $C_1$–$C_4$ alkyl, phenyl, substituted phenyl, or a phenylalkyl substituent in which the phenyl ring may be optionally substituted; p is 2 or 3; $R_9$ and $R_{10}$ are each independently represented by a $C_1$–$C_4$ alkyl or together with the nitrogen atom to which they are attached form a a ring —$CH_2$—$CH_2$—$Z_1$—$CH_2$—$CH_2$— wherein $Z_1$ is a bond, O, S, or $NR_{11}$ in which $R_{11}$ is hydrogen or $C_1$–$C_4$ alkyl; such rings include but are not limited to piperidino, morpholino, thiomorpholino, piperazino, N-methylpiperazino, or pyrrolidino;

e) the term "physiologically acceptable amide" refers to any non-toxic amide or any prodrug that allows the compounds of this application to function as NMDA antagonists: these physiologically acceptable amides may be chosen from, but are not limited to, compounds wherein X and Y may each independently be represented by —$NR_{12}R_{13}$; $R_{12}$ is represented by hydrogen or a $C_1$–$C_4$ alkyl, and $R_{13}$ is represented by hydrogen, phenyl, substituted phenyl, phenylalkyl, or a $C_1$–$C_4$ alkyl; or $R_{12}$ and $R_{13}$ are taken together with the nitrogen atom to which they are attached form a ring —$CH_2$—$CH_2$—$Z_2$—$CH_2$—$CH_2$— wherein $Z_2$ is a bond, O, S, or $NR_{14}$ in which $R_{14}$ is hydrogen or $C_1$–$C_4$ alkyl; such rings include but are not limited to piperidino, morpholino, thiomorpholino, piperazino, N-methylpiperazino, or pyrrolidino;

f) the term "phenyl" or "Ph" refers to a phenyl moiety ($C_6H_5$) of the formula;

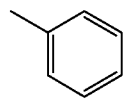

g) the term "substituted phenyl" refers to a phenyl moiety of the formula

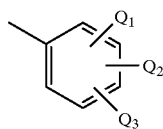

which may have from 1 to 3 substituents, $Q_1$, $Q_2$, $Q_3$ each independently chosen from the group: hydrogen, halogens, $C_1$–$C_4$ alkyl, $C_1$–$C_4$ alkoxy, —$CF_3$, —$OCF_3$, —OH, —CN, and —$NO_2$. These substituents may be the same or different and may be located at any of the ortho, meta, or para positions;

h) the term "phenylalkyl substituent" or "phenylalkyl" refers to the following structure, —$(CH_2)_m$—$C_6H_xZ_y$, in which m is an integer from 1–3. This phenyl ring may be substituted in the manner described in (g);

i) the designation "⁓" refers to a bond for which the stereochemistry is not designated.

j) as used in the preparations and examples; the term "mg" refers to milligrams; the term "g" refers to grams; the term "kg" refers to kilograms; the term "mmol" refers to millimoles; the term "mol" refers to moles; the term "mL" refers to milliliters; the term "L" refers to liters; the term "° C." refers to degrees Celsius; the term "mp" refers to melting point; the term "dec" refers to decomposition; the term "$R_f$" refers to retention factor; the term "M" refers to molar; the term "psi" refers to pounds per square inch; the term "brine" refers to a saturated aqueous solution of sodium chloride;

k) the term "pharmaceutically acceptable addition salts" refers to either an acid addition salt or a basic addition salt;

The expression "pharmaceutically acceptable acid addition salts" is intended to apply to any non-toxic organic or inorganic acid addition salt of the base compounds represented by Formula (1) or any of its intermediates. Illustrative inorganic acids which form suitable salts include hydrochloric, hydrobromic, sulfuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by the formula (1) or any of its intermediates. Illustrative bases which form suitable salts include alkali metals or alkaline-earth metals hydroxides such as, sodium, potassium, calcium, magnesium, or barium hydroxides; ammonia and aliphatic, cyclic, or aromatic organic amines such as methylamine, dimethylamine, trimethylamine, and picoline.

The compounds of formula (1) exist as geometric isomers. Any reference in this application to one of the compounds of formula (1) is meant to encompass either a specific geometrical isomer or a mixture of isomers. The specific isomers can be separated and recovered by techniques known in the art such as chromatography, and selective crystallization.

As with any group of structurally related compounds which possesses a particular generic utility, certain groups and configurations are preferred for the compounds of formula (1) in their end-use application.

Preferred embodiments of formula (1) are given below:

1) Compounds wherein X is hydroxy, $C_1$–$C_4$ alkoxy, or $NH_2$ are preferred;
2) Compounds wherein X is hydroxy, methoxy, ethoxy, or $NH_2$ are more preferred;
3) Compounds wherein X is hydroxy are most preferred;
4) Compounds wherein Y is hydroxy, $C_1$–$C_4$ alkoxy, or $NH_2$ are preferred;
5) Compounds wherein Y is hydroxy, methoxy, ethoxy, or $NH_2$ are more preferred;
6) Compounds wherein Y is hydroxy are most preferred;
7) Compounds wherein $R_1$ is hydrogen are preferred;
8) Compounds wherein —$NR_1R_2$ is in the 3-position are preferred;
9) Compounds wherein $R_2$ is a radical chosen from the group consisting of

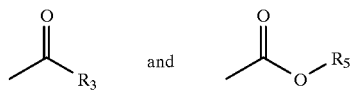

wherein $R_3$, and $R_5$ are as defined herein are preferred.

It is understood that further preferred embodiments of formula (1) can be selected by requiring one or more of the preferred embodiments 1 through 9 of formula (1) or by reference to examples given herein.

Illustrative examples of compounds encompassed by formula (1) include the following. It is understood that the examples encompass both the (E)-isomer and the (Z)-isomer of the compound and mixtures thereof. This list is meant to be representative only and is not intended to limit the scope of the invention in any way:

2-(3-Acetamidophenyl)-3-(2-carboethoxy-4,6-dichloroindol-3-yl)-propenoic acid, methyl ester;

2-(3-Propionamidophenyl)-3-(2-carboethoxy-4,6-dichloroindol-3-yl)-propenoic acid, methyl ester;

2-(3-Butyroamidophenyl)-3-(2-carboethoxy-4,6-dichloroindol-3-yl)-propenoic acid, methyl ester;

2-(3-Benzamidophenyl)-3-(2-carboethoxy-4,6-dichloroindol-3-yl)-propenoic acid, methyl ester;

2-(3-(N-Carbomethyloxyamino)phenyl)-3-(2-carboethoxy-4,6-dichloroindol-3-yl)-propenoic acid, methyl ester;

2-(3-(N-Carboethyloxyamino)phenyl)-3-(2-carboethoxy-4,6-dichloroindol-3-yl)-propenoic acid, methyl ester;

2-(3-(N-Carbopropyloxyamino)phenyl)-3-(2-carboethoxy-4,6-dichloroindol-3-yl)-propenoic acid, methyl ester;

2-(3-(N-Carboisopropyloxyamino)phenyl)-3-(2-carboethoxy-4,6-dichloroindol-3-yl)-propenoic acid, methyl ester;

2-(3-(N-Carbobutyloxyamino)phenyl)-3-(2-carboethoxy-4,6-dichloroindol-3-yl)-propenoic acid, methyl ester;

2-(3-Methylsulfonylamidophenyl)-3-(2-carboethoxy-4,6-dichloroindol-3-yl)-propenoic acid, methyl ester;

2-(3-Ethylsulfonylamidophenyl)-3-(2-carboethoxy-4,6-dichloroindol-3-yl)-propenoic acid, methyl ester;

2-(3-Propylsulfonylamidophenyl)-3-(2-carboethoxy-4,6-dichloroindol-3-yl)-propenoic acid, methyl ester;

2-(3-Butylsulfonylamidophenyl)-3-(2-carboethoxy-4,6-dichloroindol-3-yl)-propenoic acid, methyl ester;

2-(3-Benzenesulfonylamidophenyl)-3-(2-carboethoxy-4,6-dichloroindol-3-yl)-propenoic acid, methyl ester;

2-(4-Acetamidophenyl)-3-(2-carboethoxy-4,6-dichloroindol-3-yl)-propenoic acid, methyl ester;

2-(4-Benzamidophenyl)-3-(2-carboethoxy-4,6-dichloroindol-3-yl)-propenoic acid, methyl ester;

2-(4-(N-Carbomethyloxyamino)phenyl)-3-(2-carboethoxy-4,6-dichloroindol-3-yl)-propenoic acid, methyl ester;

2-(4-(N-Carboethyloxyamino)phenyl)-3-(2-carboethoxy-4,6-dichloroindol-3-yl)-propenoic acid, methyl ester;

2-(4-(N-Carboisopropyloxyamino)phenyl)-3-(2-carboethoxy-4,6-dichloroindol-3-yl)-propenoic acid, methyl ester;

2-(4-Methylsulfonylamidophenyl)-3-(2-carboethoxy-4,6-dichloroindol-3-yl)-propenoic acid, methyl ester;

2-(4-Benzenesulfonylamidophenyl)-3-(2-carboethoxy-4,6-dichloroindol-3-yl)-propenoic acid, methyl ester;

2-(2-Acetamidophenyl)-3-(2-carboethoxy-4,6-dichloroindol-3-yl)-propenoic acid, methyl ester;

2-(2-Benzamidophenyl)-3-(2-carboethoxy-4,6-dichloroindol-3-yl)-propenoic acid, methyl ester;

2-(2-(N-Carbomethyloxyamino)phenyl)-3-(2-carboethoxy-4,6-dichloroindol-3-yl)-propenoic acid, methyl ester;

2-(2-(N-Carboethyloxyamino)phenyl)-3-(2-carboethoxy-4,6-dichloroindol-3-yl)-propenoic acid, methyl ester;

2-(2-(N-Carboisopropyloxyamino)phenyl)-3-(2-carboethoxy-4,6-dichloroindol-3-yl)-propenoic acid, methyl ester;

2-(2-Methylsulfonylamidophenyl)-3-(2-carboethoxy-4,6-dichloroindol-3-yl)-propenoic acid, methyl ester;

2-(2-Benzenesulfonylamidophenyl)-3-(2-carboethoxy-4,6-dichloroindol-3-yl)-propenoic acid, methyl ester;

2-(3-Acetamidophenyl)-3-(2-carboethoxy-4,6-dichloroindol-3-yl)-propenoic acid, ethyl ester;

2-(3-Propionamidophenyl)-3-(2-carboethoxy-4,6-dichloroindol-3-yl)-propenoic acid, ethyl ester;

2-(3-Butyroamidophenyl)-3-(2-carboethoxy-4,6-dichloroindol-3-yl)-propenoic acid, ethyl ester;

2-(3-Benzamidophenyl)-3-(2-carboethoxy-4,6-dichloroindol-3-yl)-propenoic acid, ethyl ester;

2-(3-(N-Carbomethyloxyamino)phenyl)-3-(2-carboethoxy-4,6-dichloroindol-3-yl)-propenoic acid, ethyl ester;

2-(3-(N-Carboethyloxyamino)phenyl)-3-(2-carboethoxy-4,6-dichloroindol-3-yl)-propenoic acid, ethyl ester;

2-(3-(N-Carbopropyloxyamino)phenyl)-3-(2-carboethoxy-4,6-dichloroindol-3-yl)-propenoic acid, ethyl ester;

2-(3-(N-Carboisopropyloxyamino)phenyl)-3-(2-carboethoxy-4,6-dichloroindol-3-yl)-propenoic acid, ethyl ester;

2-(3-(N-Carbobutyloxyamino)phenyl)-3-(2-carboethoxy-4,6-dichloroindol-3-yl)-propenoic acid, ethyl ester;

2-(3-Methylsulfonylamidophenyl)-3-(2-carboethoxy-4,6-dichloroindol-3-yl)-propenoic acid, ethyl ester;

2-(3-Ethylsulfonylamidophenyl)-3-(2-carboethoxy-4,6-dichloroindol-3-yl)-propenoic acid, ethyl ester;

2-(3-Propylsulfonylamidophenyl)-3-(2-carboethoxy-4,6-dichloroindol-3-yl)-propenoic acid, ethyl ester;

2-(3-Butylsulfonylamidophenyl)-3-(2-carboethoxy-4,6-dichloroindol-3-yl)-propenoic acid, ethyl ester;

2-(3-Benzenesulfonylamidophenyl)-3-(2-carboethoxy-4,6-dichloroindol-3-yl)-propenoic acid, ethyl ester;

2-(4-Acetamidophenyl)-3-(2-carboethoxy-4,6-dichloroindol-3-yl)-propenoic acid, ethyl ester;

2-(4-Benzamidophenyl)-3-(2-carboethoxy-4,6-dichloroindol-3-yl)-propenoic acid, ethyl ester;

2-(4-(N-Carbomethyloxyamino)phenyl)-3-(2-carboethoxy-4,6-dichloroindol-3-yl)-propenoic acid, ethyl ester;

2-(4-(N-Carboethyloxyamino)phenyl)-3-(2-carboethoxy-4,6-dichloroindol-3-yl)-propenoic acid, ethyl ester;

2-(4-(N-Carboisopropyloxyamino)phenyl)-3-(2-carboethoxy-4,6-dichloroindol-3-yl)-propenoic acid, ethyl ester;

2-(4-Methylsulfonylamidophenyl)-3-(2-carboethoxy-4,6-dichloroindol-3-yl)-propenoic acid, ethyl ester;

2-(4-Benzenesulfonylamidophenyl)-3-(2-carboethoxy-4,6-dichloroindol-3-yl)-propenoic acid, ethyl ester;

2-(2-Acetamidophenyl)-3-(2-carboethoxy-4,6-dichloroindol-3-yl)-propenoic acid, ethyl ester;

2-(2-Benzamidophenyl)-3-(2-carboethoxy-4,6-dichloroindol-3-yl)-propenoic acid, ethyl ester;

2-(2-(N-Carbomethyloxyamino)phenyl)-3-(2-carboethoxy-4,6-dichloroindol-3-yl)-propenoic acid, ethyl ester;

2-(2-(N-Carboethyloxyamino)phenyl)-3-(2-carboethoxy-4,6-dichloroindol-3-yl)-propenoic acid, ethyl ester;

2-(2-(N-Carboisopropyloxyamino)phenyl)-3-(2-carboethoxy-4,6-dichloroindol-3-yl)-propenoic acid, ethyl ester;

2-(2-Methylsulfonylamidophenyl)-3-(2-carboethoxy-4,6-dichloroindol-3-yl)-propenoic acid, ethyl ester;

2-(2-Benzenesulfonylamidophenyl)-3-(2-carboethoxy-4,6-dichloroindol-3-yl)-propenoic acid, ethyl ester;

2-(3-Acetamidophenyl)-3-(4,6-dichloroindol-3-yl-2-carboxylic acid)-propenoic acid;

2-(3-Propionamidophenyl)-3-(4,6-dichloroindol-3-yl-2-carboxylic acid)-propenoic acid;

2-(3-Butyroamidophenyl)-3-(4,6-dichloroindol-3-yl-2-carboxylic acid)-propenoic acid;

2-(3-Benzamidophenyl)-3-(4,6-dichloroindol-3-yl-2-carboxylic acid)-propenoic acid;

2-(3-(4-Methoxybenzamido)phenyl)-3-(4,6-dichloroindol-3-yl-2-carboxylic acid)-propenoic acid;

2-(3-(4-Chlorobenzamido)phenyl)-3-(4,6-dichloroindol-3-yl-2-carboxylic acid)-propenoic acid;

2-(3-(4-Methylbenzamido)phenyl)-3-(4,6-dichloroindol-3-yl-2-carboxylic acid)-propenoic acid;

2-(3-(4-Flurorbenzamido)phenyl)-3-(4,6-dichloroindol-3-yl-2-carboxylic acid)-propenoic acid;

2-(3-(4-Triflurobenzamido)phenyl)-3-(4,6-dichloroindol-3-yl-2-carboxylic acid)-propenoic acid;

2-(3-(N-Carbomethyloxyamino)phenyl)-3-(4,6-dichloroindol-3-yl-2-carboxylic acid)-propenoic acid;

2-(3-(N-Carboethyloxyamino)phenyl)-3-(4,6-dichloroindol-3-yl-2-carboxylic acid)-propenoic acid;

2-(3-(N-Carbopropyloxyamino)phenyl)-3-(4,6-dichloroindol-3-yl-2-carboxylic acid)-propenoic acid;

2-(3-(N-Carboisopropyloxyamino)phenyl)-3-(4,6-dichloroindol-3-yl-2-carboxylic acid)-propenoic acid;

2-(3-(N-Carbobutyloxyamino)phenyl)-3-(4,6-dichloroindol-3-yl-2-carboxylic acid)-propenoic acid;

2-(3-Methylsulfonylamidophenyl)-3-(4,6-dichloroindol-3-yl-2-carboxylic acid)-propenoic acid;

2-(3-Ethylsulfonylamidophenyl)-3-(4,6-dichloroindol-3-yl-2-carboxylic acid)-propenoic acid;

2-(3-Propylsulfonylamidophenyl)-3-(4,6-dichloroindol-3-yl-2-carboxylic acid)-propenoic acid;

2-(3-Butylsulfonylamidophenyl)-3-(4,6-dichloroindol-3-yl-2-carboxylic acid)-propenoic acid;

2-(3-Benzenesulfonylamidophenyl)-3-(4,6-dichloroindol-3-yl-2-carboxylic acid)-propenoic acid;

2-(3-(4-Methoxybenzenesulfonylamido)phenyl)-3-(4,6-dichloroindol-3-yl-2-carboxylic acid)-propenoic acid;

2-(3-(4-Chlorobenzenesulfonylamido)phenyl)-3-(4,6-dichloroindol-3-yl-2-carboxylic acid)-propenoic acid;

2-(3-Acetamidophenyl)-3-(4,6-dichloroindol-3-yl-2-carboxylic acid)-propenoic acid amide;

2-(3-Propionamidophenyl)-3-(4,6-dichloroindol-3-yl-2-carboxylic acid)-propenoic acid amide;

2-(3-Butyroamidophenyl)-3-(4,6-dichloroindol-3-yl-2-carboxylic acid)-propenoic acid amide;

2-(3-Benzamidophenyl)-3-(4,6-dichloroindol-3-yl-2-carboxylic acid)-propenoic acid amide;

2-(3-(4-Methoxybenzamido)phenyl)-3-(4,6-dichloroindol-3-yl-2-carboxylic acid)-propenoic acid amide;

2-(3-(4-Chlorobenzamido)phenyl)-3-(4,6-dichloroindol-3-yl-2-carboxylic acid)-propenoic acid amide;

2-(3-(4-Methylbenzamido)phenyl)-3-(4,6-dichloroindol-3-yl-2-carboxylic acid)-propenoic acid amide;

2-(3-(4-Flurorbenzamido)phenyl)-3-(4,6-dichloroindol-3-yl-2-carboxylic acid)-propenoic acid amide;

2-(3-(4-Triflurobenzamido)phenyl)-3-(4,6-dichloroindol-3-yl-2-carboxylic acid)-propenoic acid amide;

2-(3-(N-Carbomethyloxyamino)phenyl)-3-(4,6-dichloroindol-3-yl-2-carboxylic acid)-propenoic acid amide;

2-(3-(N-Carboethyloxyamino)phenyl)-3-(4,6-dichloroindol-3-yl-2-carboxylic acid)-propenoic acid amide;

2-(3-(N-Carbopropyloxyamino)phenyl)-3-(4,6-dichloroindol-3-yl-2-carboxylic acid)-propenoic acid amide;

2-(3-(N-Carboisopropyloxyamino)phenyl)-3-(4,6-dichloroindol-3-yl-2-carboxylic acid)-propenoic acid amide;

2-(3-(N-Carbobutyloxyamino)phenyl)-3-(4,6-dichloroindol-3-yl-2-carboxylic acid)-propenoic acid amide;

2-(3-Methylsulfonylamidophenyl)-3-(4,6-dichloroindol-3-yl-2-carboxylic acid)-propenoic acid amide;

2-(3-Ethylsulfonylamidophenyl)-3-(4,6-dichloroindol-3-yl-2-carboxylic acid)-propenoic acid amide;

2-(3-Propylsulfonylamidophenyl)-3-(4,6-dichloroindol-3-yl-2-carboxylic acid)-propenoic acid amide;

2-(3-Butylsulfonylamidophenyl)-3-(4,6-dichloroindol-3-yl-2-carboxylic acid)-propenoic acid amide;

2-(3-Benzenesulfonylamidophenyl)-3-(4,6-dichloroindol-3-yl-2-carboxylic acid)-propenoic acid amide;

2-(3-(4-Methoxybenzenesulfonylamido)phenyl)-3-(4,6-dichloroindol-3-yl-2-carboxylic acid)-propenoic acid amide;

2-(3-(4-Chlorobenzenesulfonylamido)phenyl)-3-(4,6-dichloroindol-3-yl-2-carboxylic acid)-propenoic acid amide;

2-(4-Acetamidophenyl)-3-(4,6-dichloroindol-3-yl-2-carboxylic acid)-propenoic acid;

2-(4-Propionamidophenyl)-3-(4,6-dichloroindol-3-yl-2-carboxylic acid)-propenoic acid;

2-(4-Butyroamidophenyl)-3-(4,6-dichloroindol-3-yl-2-carboxylic acid)-propenoic acid;

2-(4-Benzamidophenyl)-3-(4,6-dichloroindol-3-yl-2-carboxylic acid)-propenoic acid;

2-(4-(N-Carbomethyloxyamino)phenyl)-3-(4,6-dichloroindol-3-yl-2-carboxylic acid)-propenoic acid;

2-(4-(N-Carboethyloxyamino)phenyl)-3-(4,6-dichloroindol-3-yl-2-carboxylic acid)-propenoic acid;

2-(4-(N-Carbopropyloxyamino)phenyl)-3-(4,6-dichloroindol-3-yl-2-carboxylic acid)-propenoic acid;

2-(4-(N-Carboisopropyloxyamino)phenyl)-3-(4,6-dichloroindol-3-yl-2-carboxylic acid)-propenoic acid;

2-(4-Methylsulfonylamidophenyl)-3-(4,6-dichloroindol-3-yl-2-carboxylic acid)-propenoic acid;

2-(4-Benzenesulfonylamidophenyl)-3-(4,6-dichloroindol-3-yl-2-carboxylic acid)-propenoic acid;

2-(2-Acetamidophenyl)-3-(4,6-dichloroindol-3-yl-2-carboxylic acid)-propenoic acid;

2-(2-Benzamidophenyl)-3-(4,6-dichloroindol-3-yl-2-carboxylic acid)-propenoic acid;

2-(2-(N-Carbomethyloxyamino)phenyl)-3-(4,6-dichloroindol-3-yl-2-carboxylic acid)-propenoic acid;

2-(2-(N-Carboethyloxyamino)phenyl)-3-(4,6-dichloroindol-3-yl-2-carboxylic acid)-propenoic acid;

2-(2-(N-Carbopropyloxyamino)phenyl)-3-(4,6-dichloroindol-3-yl-2-carboxylic acid)-propenoic acid;

2-(2-(N-Carboisopropyloxyamino)phenyl)-3-(4,6-dichloroindol-3-yl-2-carboxylic acid)-propenoic acid;

2-(2-Methylsulfonylamidophenyl)-3-(4,6-dichloroindol-3-yl-2-carboxylic acid)-propenoic acid;

2-(2-Benzenesulfonylamidophenyl)-3-(4,6-dichloroindol-3-yl-2-carboxylic acid)-propenoic acid;

2-(3-Acetamidophenyl)-3-(5,6-dichloroindol-3-yl-2-carboxylic acid)-propenoic acid;

2-(3-Benzamidophenyl)-3-(5,6-dichloroindol-3-yl-2-carboxylic acid)-propenoic acid;

2-(3-(N-Carbomethyloxyamino)phenyl)-3-(5,6-dichloroindol-3-yl-2-carboxylic acid)-propenoic acid;

2-(3-(N-Carboethyloxyamino)phenyl)-3-(5,6-dichloroindol-3-yl-2-carboxylic acid)-propenoic acid;

2-(3-(N-Carbopropyloxyamino)phenyl)-3-(5,6-dichloroindol-3-yl-2-carboxylic acid)-propenoic acid;

2-(3-(N-Carboisopropyloxyamino)phenyl)-3-(5,6-dichloroindol-3-yl-2-carboxylic acid)-propenoic acid;

2-(3-Methylsulfonylamidophenyl)-3-(5,6-dichloroindol-3-yl-2-carboxylic acid)-propenoic acid;

2-(3-Benzenesulfonylamidophenyl)-3-(5,6-dichloroindol-3-yl-2-carboxylic acid)-propenoic acid;

2-(3-Acetamidophenyl)-3-(6-chloroindol-3-yl-2-carboxylic acid)-propenoic acid;

2-(3-Benzamidophenyl)-3-(6-chloroindol-3-yl-2-carboxylic acid)-propenoic acid;

2-(3-(N-Carbomethyloxyamino)phenyl)-3-(6-chloroindol-3-yl-2-carboxylic acid)-propenoic acid;

2-(3-(N-Carboethyloxyamino)phenyl)-3-(6-chloroindol-3-yl-2-carboxylic acid)-propenoic acid;

2-(3-(N-Carbopropyloxyamino)phenyl)-3-(6-chloroindol-3-yl-2-carboxylic acid)-propenoic acid;

2-(3-(N-Carboisopropyloxyamino)phenyl)-3-(6-chloroindol-3-yl-2-carboxylic acid)-propenoic acid;

2-(3-Methylsulfonylamidophenyl)-3-(6-chloroindol-3-yl-2-carboxylic acid)-propenoic acid;

2-(3-Benzenesulfonylamidophenyl)-3-(6-chloroindol-3-yl-2-carboxylic acid)-propenoic acid;

2-(3-Acetamidophenyl)-3-(indol-3-yl-2-carboxylic acid)-propenoic acid;

2-(3-(N-Carbomethyloxyamino)phenyl)-3-(indol-3-yl-2-carboxylic acid)-propenoic acid;

2-(3-Methylsulfonylamidophenyl)-3-(indol-3-yl-2-carboxylic acid)-propenoic acid;

2-(3-Benzenesulfonylamidophenyl)-3-(indol-3-yl-2-carboxylic acid)-propenoic acid;

2-(3-Acetamidophenyl)-3-(7-ethyl-5-bromoindol-3-yl-2-carboxylic acid)-propenoic acid;

2-(3-Benzamidophenyl)-3-(7-ethyl-5-bromoindol-3-yl-2-carboxylic acid)-propenoic acid;

2-(3-(N-Carbomethyloxyamino)phenyl)-3-(7-ethyl-5-bromoindol-3-yl-2-carboxylic acid)-propenoic acid;

2-(3-(N-Carboethyloxyamino)phenyl)-3-(7-ethyl-5-bromoindol-3-yl-2-carboxylic acid)-propenoic acid;

2-(3-(N-Carbopropyloxyamino)phenyl)-3-(7-ethyl-5-bromoindol-3-yl-2-carboxylic acid)-propenoic acid;

2-(3-(N-Carboisopropyloxyamino)phenyl)-3-(7-ethyl-5-bromoindol-3-yl-2-carboxylic acid)-propenoic acid;

2-(3-Methylsulfonylamidophenyl)-3-(7-ethyl-5-bromoindol-3-yl-2-carboxylic acid)-propenoic acid;

2-(3-Benzenesulfonylamidophenyl)-3-(7-ethyl-5-bromoindol-3-yl-2-carboxylic acid)-propenoic acid;

2-(3-Acetamidophenyl)-3-(5-ethyl-7-bromoindol-3-yl-2-carboxylic acid)-propenoic acid;

2-(3-Benzamidophenyl)-3-(5-ethyl-7-bromoindol-3-yl-2-carboxylic acid)-propenoic acid;

2-(3-(N-Carbomethyloxyamino)phenyl)-3-(5-ethyl-7-bromoindol-3-yl-2-carboxylic acid)-propenoic acid;

2-(3-(N-Carboethyloxyamino)phenyl)-3-(5-ethyl-7-bromoindol-3-yl-2-carboxylic acid)-propenoic acid;

2-(3-(N-Carbopropyloxyamino)phenyl)-3-(5-ethyl-7-bromoindol-3-yl-2-carboxylic acid)-propenoic acid;

2-(3-(N-Carboisopropyloxyamino)phenyl)-3-(5-ethyl-7-bromoindol-3-yl-2-carboxylic acid)-propenoic acid;

2-(3-Methylsulfonylamidophenyl)-3-(5-ethyl-7-bromoindol-3-yl-2-carboxylic acid)-propenoic acid;

2-(3-Benzenesulfonylamidophenyl)-3-(5-ethyl-7-bromoindol-3-yl-2-carboxylic acid)-propenoic acid;

2-(3-Acetamidophenyl)-3-(5-fluoro-7-chloroindol-3-yl-2-carboxylic acid)-propenoic acid;

2-(3-Benzamidophenyl)-3-(5-fluoro-7-chloroindol-3-yl-2-carboxylic acid)-propenoic acid;

2-(3-(N-Carbomethyloxyamino)phenyl)-3-(5-fluoro-7-chloroindol-3-yl-2-carboxylic acid)-propenoic acid;

2-(3-(N-Carboethyloxyamino)phenyl)-3-(5-fluoro-7-chloroindol-3-yl-2-carboxylic acid)-propenoic acid;

2-(3-(N-Carbopropyloxyamino)phenyl)-3-(5-fluoro-7-chloroindol-3-yl-2-carboxylic acid)-propenoic acid;

2-(3-(N-Carboisopropyloxyamino)phenyl)-3-(5-fluoro-7-chloroindol-3-yl-2-carboxylic acid)-propenoic acid;

2-(3-Methylsulfonylamidophenyl)-3-(5-fluoro-7-chloroindol-3-yl-2-carboxylic acid)-propenoic acid;

2-(3-Benzenesulfonylamidophenyl)-3-(5-fluoro-7-chloroindol-3-yl-2-carboxylic acid)-propenoic acid;

2-(3-Acetamidophenyl)-3-(7-fluoro-5-chloroindol-3-yl-2-carboxylic acid)-propenoic acid;

2-(3-Benzamidophenyl)-3-(7-fluoro-5-chloroindol-3-yl-2-carboxylic acid)-propenoic acid;

2-(3-(N-Carbomethyloxyamino)phenyl)-3-(7-fluoro-5-chloroindol-3-yl-2-carboxylic acid)-propenoic acid;

2-(3-(N-Carboethyloxyamino)phenyl)-3-(7-fluoro-5-chloroindol-3-yl-2-carboxylic acid)-propenoic acid;

2-(3-(N-Carbopropyloxyamino)phenyl)-3-(7-fluoro-5-chloroindol-3-yl-2-carboxylic acid)-propenoic acid;

2-(3-(N-Carboisopropyloxyamino)phenyl)-3-(7-fluoro-5-chloroindol-3-yl-2-carboxylic acid)-propenoic acid;

2-(3-Methylsulfonylamidophenyl)-3-(7-fluoro-5-chloroindol-3-yl-2-carboxylic acid)-propenoic acid;

2-(3-Benzenesulfonylamidophenyl)-3-(7-fluoro-5-chloroindol-3-yl-2-carboxylic acid)-propenoic acid;

2-(3-Acetamidophenyl)-3-(5,7-dibromoindol-3-yl-2-carboxylic acid)-propenoic acid;

2-(3-Benzamidophenyl)-3-(5,7-dibromoindol-3-yl-2-carboxylic acid)-propenoic acid;

2-(3-(N-Carbomethyloxyamino)phenyl)-3-(5,7-dibromoindol-3-yl-2-carboxylic acid)-propenoic acid;

2-(3-(N-Carboethyloxyamino)phenyl)-3-(5,7-dibromoindol-3-yl-2-carboxylic acid)-propenoic acid;

2-(3-(N-Carbopropyloxyamino)phenyl)-3-(5,7-dibromoindol-3-yl-2-carboxylic acid)-propenoic acid;

2-(3-(N-Carboisopropyloxyamino)phenyl)-3-(5,7-dibromoindol-3-yl-2-carboxylic acid)-propenoic acid;

2-(3-Methylsulfonylamidophenyl)-3-(5,7-dibromoindol-3-yl-2-carboxylic acid)-propenoic acid;

2-(3-Benzenesulfonylamidophenyl)-3-(5,7-dibromoindol-3-yl-2-carboxylic acid)-propenoic acid.

A general synthetic procedure for preparing these compounds of formula (1) is set forth in Reaction Scheme 1. In Reaction Scheme 1, the reagents and starting materials are readily available to one of ordinary skill in the art. In Reaction Scheme 1, all substituents, unless otherwise indicated, are as previously defined.

REACTION SCHEME 1

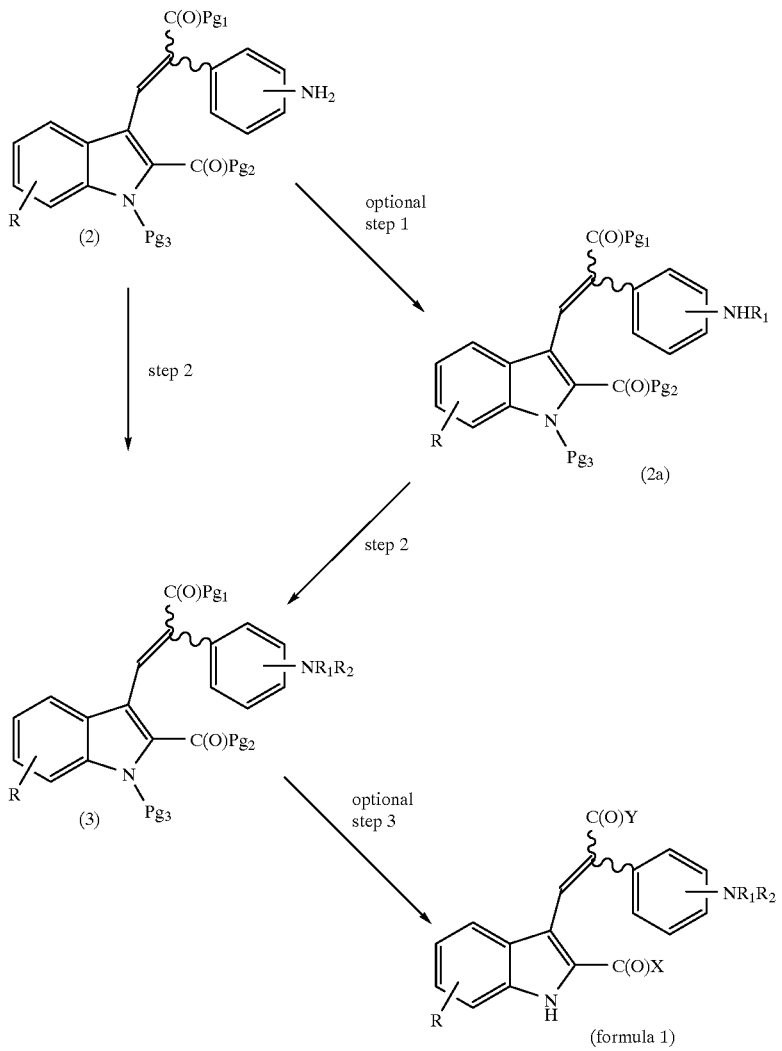

In Reaction Scheme 1, optional step 1, an appropriate 2-(aminophenyl)-3-(indol-3-yl)-propenoic acid derivative of structure (2) is alkylated to give a 2-(N-alkylaminophenyl)-3-(indol-3-yl)-propenoic acid derivative of structure (2a) in which $R_1$ is $C_1$–$C_4$ alkyl. An appropriate 2-(aminophenyl)-3-(indol-3-yl)-propenoic acid derivative of structure (2) can be alkylated by contact with an appropriate alkylating agent, reductive amination, or reduction of an acylated 2-(aminophenyl)-3-(indol-3-yl)-propenoic acid derivative of structure (3) using a suitable reducing agent.

An appropriate 2-(aminophenyl)-3-(indol-3-yl)-propenoic acid derivative of structure (2) is one in which R is as desired in the final product of formula (1), $Pg_1$ is X as desired in the final product of formula (1) or gives rise after deprotection and/or functionalization as required to X as desired in the final product of formula (1), $Pg_2$ is Y as desired in the final product of formula (1) or gives rise after deprotection and/or functionalization as required to Y as desired in the final product of formula (1), and $Pg_3$ is hydrogen or a protecting group which is removed to give a final product of formula (1) or allows for selective deprotection and functionalization as may be required to incorporate X and Y desired in the final product of formula (1). Appropriate 2-(aminophenyl)-3-(indol-3-yl)-propenoic acid derivatives of structure (2) are readily prepared as described herein and in U.S. Pat. No. 5,519,048, which is herein incorporated by reference.

An appropriate alkylating agent is one that allows for the transfer of a $C_1$–$C_4$ alkyl group. Appropriate alkylating agents include alkyl halides, for example, methyl iodide, ethyl iodide, propyl iodide, butyl iodide, ethyl bromide, propyl bromide, butyl bromide, propyl chloride, butyl chloride. An appropriate aldehyde is one that forms a $C_1$–$C_4$ alkylamine upon reductive alkylation, for example, formaldehyde, acetaldehyde, propionaldehyde, and butyraldehyde.

For example, an appropriate 2-(aminophenyl)-3-(indol-3-yl)-propenoic acid derivative of structure (2) is contacted with 1 to 2 molar equivalents of an appropriate alkyl halide. The reaction is carried out in a suitable solvent, such as chloroform, dimethylformamide, or acetonitrile. The reaction is carried out using a suitable base, such as triethylamine, diisopropylethylamine, or sodium bicarbonate. The reaction is generally carried out at temperatures of from ambient temperature to the refluxing temperature of the solvent. The reaction generally requires from 1 hour to 120 hours. The product can be isolated by techniques well known in the art, such as extraction and evaporation. The product can then be purified by techniques well known in the art, such as chromatography, trituration, or recrystallization.

Alternately, for example, an appropriate 2-(aminophenyl)-3-(indol-3-yl)-propenoic acid derivative of structure (2) is contacted with an appropriate aldehyde in a reductive amination. Reductive aminations using amines and aldehydes are well known and appreciated in the art. The reaction is carried out using a molar excess of sodium borohydride or sodium cyanoborohydride with sodium cyanoborohydride being preferred. The reaction is carried out in a suitable solvent, such as methanol, dimethylformamide, or ethanol. The pH of the reaction mixture may require adjustment as described in R. F. Borch et al, *J. Am. Chem. Soc.* 2897–2904 (1971). The reaction is carried out at temperatures of from 0° C. to 50° C. The reaction generally requires 2 to 24 hours. The product can be isolated and purified by techniques well known in the art, such as extraction, evaporation, chromatography, and recrystallization.

Alternately, a 2-(N-alkylaminophenyl)-3-(indol-3-yl)-propenoic acid derivative of structure (2a) in which $R_1$ is $C_1$–$C_4$ alkyl can be prepared by reduction of an appropriate acylated 2-(aminophenyl)-3-(indol-3-yl)-propenoic acid derivative of structure (3) wherein $R_2$ is formyl, acetyl, propionyl, butyryl, and the like. An appropriate acylated 2-(aminophenyl)-3-(indol-3-yl)-propenoic acid derivative of structure (3) can be prepared as described in Reaction Scheme 1, step 2, below. For example, acylated 2-(aminophenyl)-3-(indol-3-yl)-propenoic acid derivative of structure (3) wherein $R_2$ is formyl, acetyl, propionyl, and butyryl can be reduced to give the N-methyl, N-ethyl, N-propyl, and N-butyl derivatives, respectively, of 2-(N-alkylaminophenyl)-3-(indol-3-yl)-propenoic acid derivatives. The reaction is carried out using a molar excess of a suitable reducing agent, such as borane or a borane complex, such as borane dimethylsulfide. The reaction is carried out using a suitable solvent, such as diethyl ether or tetrahydrofuran. The reaction is carried out at temperatures of from ambient temperatures to the refluxing temperature of the solvent. The reaction generally requires 2 to 48 hours. The product can be isolated and purified by techniques well known in the art, such as quenching, extraction, evaporation, chromatography, and recrystallization.

In Reaction Scheme 1, step 2, an appropriate 2-(aminophenyl)-3-(indol-3-yl)-propenoic acid derivative of structure (2) or an appropriate 2-(N-alkylaminophenyl)-3-(indol-3-yl)-propenoic acid derivative of structure (2a) is contacted with an appropriate acylating agent, sulfonating agent, or carbamoylating agent to give a 2-(amidophenyl)-3-(indol-3-yl)-propenoic acid derivative of structure (3).

An appropriate 2-(aminophenyl)-3-(indol-3-yl)-propenoic acid derivative of structure (2) or an appropriate 2-(N-alkylaminophenyl)-3-(indol-3-yl)-propenoic acid derivative of structure (2a) is as described in Reaction Scheme 1, optional step 1, above. Appropriate acylating agents, sulfonating agents, and carbamoylating agents are ones that transfer the group $R_2$ as is desired in the final product of formula (1).

Appropriate acylating agents include acid halides, acid anhydrides, and activated esters of formic acid, $C_1$–$C_4$ alkyl carboxylic acids, benzoic acid, and substituted benzoic acid, for example formic acid acetic acid anhydride, acetic acid anhydride, acetyl chloride, acetyl bromide, n-propionic chloride, isoproponic chloride, n-butyryl chloride, s-butyryl chloride, t-butyryl, acetyl-O-hydroxysuccinate and the like, and benzoyl chloride, benzoyl bromide, 4-fluorobenzoyl chloride, 4-chlorobenzoyl chloride, 4-bromobenzoyl chloride, 4-trifluoromethylbenzoyl chloride, 4-methylbenzoyl chloride, 4-methyoxybenzoyl chloride, 3,4-dimethoxybenzoyl chloride, 3,4,5-trimethoxybenzoyl chloride, 2,4-dichlorobenzoyl chloride, and the like.

Appropriate sulfonating agents include $C_1$–$C_4$ alkylsulfonyl chlorides, benzenesulfonyl chlorides and substituted benzenesulfonyl chlorides for example, methanesulfonyl chloride, ethanesulfonyl chloride, propanesulfonyl chloride, butanesulfonyl chloride, benzenesulfonyl chloride, 4-methoxybenzenesulfonyl chloride, 4-chlorobenzenesulfonyl chloride, 4-methylbenzenesulfonyl chloride, 4-trifluormethylbenzenesulfonyl chloride, and the like.

Appropriate carbamoylating agents include $C_1$–$C_4$ alkyl chloroformates, for example, methyl chloroformate, ethyl chloroformate, n-propyl chloroformate, isopropyl chloroformate, n-butyl chloroformate, s-butyl chloroformate, t-butyl chloroformate, and the like.

For example, an appropriate 2-(aminophenyl)-3-(indol-3-yl)-propenoic acid derivative of structure (2) or an appropriate 2-(N-alkylaminophenyl)-3-(indol-3-yl)-propenoic acid derivative of structure (2a) is contacted with an appropriate acylating agent, sulfonating agent, or carbamoylating agent. The reaction is carried out in a suitable solvent, such as tetrahydrofuran, dichloromethane, chloroform, dimethylformamide, or acetonitrile. The reaction is carried out using a suitable base, such as piperidine, pyridine, N-methylmorpholine, triethylamine, diisopropylethylamine, potassium carbonate, potassium bicarbonate, sodium bicarbonate, or sodium carbonate. The reaction is generally carried out at temperatures of from ambient temperature to the refluxing temperature of the solvent. The reaction generally requires from 1 hour to 120 hours. The product can be isolated by techniques well known in the art, such as extraction and evaporation. The product can then be purified by techniques well known in the art, such as chromatography, trituration, or recrystallization.

In Reaction Scheme 1, optional step 3, the product of structure (3) may be deprotected and/or functionalized using techniques well known in the art to give compounds of formula (1). These techniques include hydrolysis of esters, selective hydrolysis of esters, transesterification, amidation of activated ester leaving groups, and esterification of activated ester leaving groups.

As is disclosed in Reaction Scheme 1, the compounds of formula (1) can be prepared by submitting a compound (3) to an appropriate functionalization reaction which introduces the appropriate functionality at the 2-position of the indole nucleus and/or at the 1-position of the propenoic acid thereby producing the desired compound of formula (1).

The functionalization reactions can be carried out using techniques well known in the art. For example, ester functionalities can be added to the 2-position of the indole nucleus and/or at the 1-position of the propenoic acid utilizing a variety of esterification techniques. One suitable esterification technique comprises contacting the appropriate compound of structure (3) in which $Pg_1$ and $Pg_2$ are $C_1$–$C_4$ alkyl functions with an excess of an alcohol of the formula XOH or YOH in which X and Y are the same as defined for formula (1). The reaction is typically carried out in the presence of an excess of a base such as potassium carbonate. The reaction is typically carried out at a temperature ranging from room temperature to reflux for a period of time ranging from 1 hour to 24 hours. The product can be isolated and purified by techniques well known in the art, such as quenching, extraction, evaporation, chromatography, and recrystallization.

Amides can also be easily be prepared by contacting a compound of structure (3) in which $Pg_1$ and $Pg_2$ are $C_1$–$C_4$ alkyls with an excess of ammonia or a mono- or dialkylamine corresponding to the desired X or Y substituent at a temperature of from 0–100° C. for a period of time ranging from 1–48 hours using the amine as solvent or in an inert solvent such as tetrahydrofuran. The resulting amide derivatives of formula (1) can then be isolated and purified by techniques known in the art, such as extraction, evaporation, chromatography, and recrystallization.

Alternately, amide can be formed by the use of active ester leaving groups. The formation and use of active ester leaving groups used in functionalization reactions is well known and appreciated in the art. Active ester leaving groups include but are not limited to anhydrides, mixed anhydrides, acid chlorides, acid bromides, 1-hydroxybenzotriazole esters, 1-hydroxysuccinimide esters, or the activated intermediates formed in the presence of coupling reagents, such as dicyclohexylcarbodiimide, 1-(3-dimethyaminopropyl)-3-ethylcarbodiimide, and 2-ethoxy-1-ethoxycarbonyl-1,2-dihydroquinolone. Active ester leaving groups may be prepared and isolated before their use or may be prepared and used without isolation to form physiologically acceptable esters or physiologically acceptable amides.

As is readily apparent to those skilled in the art, if X and Y are not both represented by the same functionality in the final product, then it will be necessary to carry out the deprotection and the functionalization reactions in a sequential manner utilizing suitable protecting groups such as those described in *Protecting Groups in Organic Synthesis*, T. Greene. This can be done utilizing techniques known to those skilled in the art; D. B. Bryan et al, *J. Am. Chem. Soc*, 99, 2353 (1977); E. Wuensch, *Methoden der Organischen Chemie* (Houben-Weyl), E. Mueller, Ed., George Theime Verlag, Stuttgart, 1974, Vol. 15; M. G. Saulnierand and G. W. Gribble, *J. Org. Chem.,* 47, 2810 (1982); Y. Egawa et al, *Chem. Pharm. Bull.,* 7, 896 (1963); R. Adams and L. H. Ulich, *J. Am. Chem. Soc.,* 42, 599 (1920); and J Szmuszkoviocz, *J. Org. Chem.,* 29, 834 (1964).

For example, a compound of formula (1) in which Y is a physiologically acceptable amide and X is a physiologically acceptable ester or —OH can be prepared from a compound of structure (3) in which $Pg_2$ is t-butyl—O— and $Pg_1$ is a physiologically acceptable ester other than t-butyl or a hydrolyzable ester. Selective removal of the t-butyl group gives a compound of structure (3) in which $Pg_2$ is —OH and $Pg_1$ is a physiologically acceptable ester other than t-butyl— O— or a hydrolyzable ester which can be amidated through the formation of an activated ester leaving group followed by the addition of an suitable amine as is well known in the art. A suitable amine is one which gives a physiologically acceptable amide, Y, as is desired in the final product of formula (1). Suitable amines include but are not limited to ammonia, methylamine, dimethylamine, ethylamine, diethylamine, propylamine, butylamine, aniline, 4-chloroaniline, N-methylaniline, benzylamine, phenethylamine, morpholine, piperazine, piperidine, N-methylpiperazine, thiomorpholine, pyrrolidine, and N-methylbenzylamine. Formation of an active ester leaving group may require protection of the indole NH using a suitable protecting group, such as benzenesulfonyl, p-toluenesulfonyl, trimethylsilyl, trimethylsilylethoxy methyl, and the like. In cases in which the indole NH requires protection this is best done before the removal of t-butyl from $Pg_2$. Further functionalization or hydrolysis gives a compound of formula (1) in which Y is a physiologically acceptable amide and X is a physiologically acceptable ester or —OH. After the functionalization, removal of the indole NH protecting group gives a compound of formula (1).

Similarly, a compound of formula (1) in which X is a physiologically acceptable amide and Y is a physiologically acceptable ester or —OH can be prepared from a compound of structure (3) in which $Pg_1$ is t-butyl—O— and $Pg_2$ is a physiologically acceptable ester other than t-butyl—O— or a hydrolyzable ester.

The compounds of formula (1) in which X and Y are —OH can be prepared from a compound of structure (3) in which $Pg_1$ and $Pg_2$ are $C_1$–$C_4$ alkoxy, or an activated ester leaving group by deprotection using a molar excess of a suitable reagent, such as lithium hydroxide, sodium hydroxide, potassium hydroxide, sodium bicarbonate, sodium carbonate, or potassium carbonate with lithium hydroxide, sodium hydroxide, potassium hydroxide being preferred and lithium hydroxide being most preferred. These deprotections are carried out in a suitable solvent, such as methanol, ethanol, mixtures of methanol and water, mixtures of ethanol and water, mixtures of tetrahydrofuran and water, or water. The reaction is typically carried out at a temperature ranging from room temperature to reflux for a period of time ranging from 1 hour to 24 hours. After the reaction is completed, the desired product of formula (1) can be recovered by techniques well known in the art, such as evaporation, precipitation by adjustment of the pH of the solution with a suitable acid such as hydrochloric acid, acetic acid, etc., extraction, and recrystallization.

The following examples and preparations present typical syntheses of the compounds of formula (1). These examples are understood to be illustrative only and are not intended to limit the scope of the invention in any way.

PREPARATION 1.1

3-Formyl-2-carboethoxy-4,6-dichloroindole

Combine 3,5-dichlorophenylhydrazine (300 g) and ethanol (2 L). Add ethyl pyruvate (153.6 mL) and sulfuric acid (25 mL). After 3 hours, evaporate in vacuo to obtain a residue. Cover the residue with ethyl acetate and water. Add solid sodium bicarbonate until the aqueous layer is neutralized. Separate the layers and extract the aqueous layer with ethyl acetate. Combine the organic layers, dry over $MgSO_4$, filter, and evaporate in vacuo to give ethyl pyruvate-3,5-dichlorophenylhydrazone.

Combine ethyl pyruvate-3,5-dichlorophenylhydrazone (100 g) and polyphosphoric acid (2 kg). Heat on a stream bath. After 5 hours, stop the heating and slowly add ice (100 g) to thin the solution. Pour the reaction mixture onto ice to give an aqueous suspension. Extract the aqueous suspension three times with ethyl acetate. Combine the organic layers, dry over $MgSO_4$, filter, and evaporate in vacuo to give a solid. Triturate the solid with diethyl ether, filter, and dry to give 2-carboethoxy-4,6-dichloroindole.

Combine 2-carboethoxy-4,6-dichloroindole (20.0 g, 0.077 mol), and dimethylformamide (9.0 mL, 0.117 mol) in dichloroethane (100 mL). Add phosphoryl chloride (18.0 g, 0.117 mmol). Heat to reflux. After 3.5 hours, cool the reaction mixture to ambient temperature to obtain a solid. Collect the solid by filtration, rinse with dichloromethane.

Combine the solid with aqueous 1 M sodium acetate solution and stir. After 1 hour, filter, rinse with water, and dry to give the title compound.

PREPARATION 1.2
3-Formyl-2-carboethoxy-4,6-dichloroindole

Combine 2-carboethoxy-4,6-dichloroindole (10.0 g, 0.039 mol), and dimethylformamide (4.5 mL, 0.057 mol) in dichloroethane (20 mL). Add phosphoryl chloride (8.9 g, 0.058 mmol). Heat to 80° C. After 18 hours, cool the reaction mixture to ambient temperature to give a solid. Filter the solid and combine with aqueous 1 M sodium acetate solution and stir. After 18 hours, filter, rinse with water, and dry to give the title compound: mp 216–217° C.; $R_f$=0.24 (silica gel, 1/1 ether/hexane); $^1$H NMR (CDCl$_3$) δ 10.80 (s, 1 H), 9.40 (br s, 1 H), 7.39 (s, 1 H), 7.35 (s, 1 H), 4.52 (q, 2 H, J=7.2 Hz), 1.47 (t, 3 H, J=7.1 Hz).

PREPARATION 2
3-Methoxy-2-(3-nitrophenyl)-propenoic acid, methyl ester

Combine (3-nitrophenyl)acetic acid (20.0 g, 110 mmol) and anhydrous methanol (125 mL). Add 7 drops of concentrated sulfuric acid. Heat to 50° C. After 14 hours, cool to ambient temperature. Evaporate in vacuo to give a residue. Partition the residue between water and diethyl ether. Separate the organic layer and extract with aqueous saturated sodium bicarbonate solution and brine. Dry the organic layer over MgSO$_4$ and filter. Slowly evaporate to give methyl (3-nitrophenyl)acetate. $^1$H NMR (CDCl$_3$) δ 8.17 (d, 1 H, J=1.1 Hz), 8.14 (dd, 1 H, J=1.0, 7.7 Hz), 7.63 (dd, 1 H, J=1.1, 7.7 Hz), 7.52 (t, 1 H, J=7.7 Hz), 3.75 (s, 2 H), 3.73 (s, 3 H).

Combine freshly prepared sodium methoxide (9.3 g, 172 mmol) and tetrahydrofuran (125 mL). Cool to 0° C. Add methyl formate (10.6 mL, 172 mmol). Add dropwise a solution of methyl (3-nitrophenyl)acetate (15.3 g, 78.3 mmol) in tetrahydrofuran (125 mL). After the addition is complete, warm the reaction mixture to ambient temperature. After 16 hours, evaporate in vacuo to give a residue. Dissolve the residue in dimethylformamide (125 mL). Add dropwise, methyl iodide (19.5 mL, 313 mmol). After 4 hours, dilute the reaction mixture with ethyl acetate and extract with water, saturated aqueous solution of sodium thiosulfate, and brine. Dry over MgSO$_4$, filter through a plug of silica gel eluting with dichloromethane to give the title compound: mp; 101–103° C.

EXAMPLE 1
(E) and (Z)-2-(3-Nitrophenyl)-3-(2-carboethoxy-4,6-dichloroindol-3-yl)-propenoic acid, methyl ester

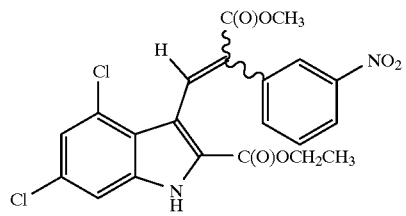

Combine 3-methoxy-2-(3-nitrophenyl)-propenoic acid, methyl ester (13.9 g, 58.8 mmol) and 1,2-dichloroethane (100 mL). Add dropwise trimethylsilyl triflate (11.4 mL, 58.5 mmol) by syringe. After 15 minutes, add portionwise 2-carboethoxy-4,6-dichloroindole (11.7 g, 45.2 mmol). Heat to 70° C. After 16 hours, cool to ambient temperature. Add aqueous saturated sodium bicarbonate solution. Extract with ethyl acetate. Separate the organic layer and extract with water and brine. Dry the organic layer over MgSO$_4$, filter, and evaporate in vacuo to give a residue. Chromatograph the residue on silica gel eluting with ⅓ ethyl acetate/hexane to give the title compound: $R_f$=0.5 (30% ethyl acetate/cyclohexane).

Separate the isomers by fractional recrystallization from ethyl acetate/cyclohexane. Initially, mainly the Z isomer precipitates as a yellow powder, which can then be recrystallized from ether/cyclohexane to obtain Z isomer: mp 178–180° C.; IR (KBr) νmax 3408, 3316, 1715, 1530, 1443, 1350, 1319, 1238, 1209, 1182 cm$^{-1}$; $^1$H NMR (DMSO-d$_6$) δ 12.46 (bs, 1 H), 8.27 (t, 1 H, J=1.9 Hz), 8.22 (dm, 1 H, J=8.2 Hz), 7.92 (dm, 1 H, J=8.0 Hz), 7.71 (t, 1 H, J=8.0 Hz), 7.60 (s, 1 H), 7.44 (d, 1 H, J=1.7 Hz), 7.17 (d, 1 H, J=1.7 Hz), 4.26 (q, 2 H, J=7.1 Hz), 3.41 (s, 3 H), 1.23 (t, 3 H, J=7.1 Hz). Elemental Analysis Calculated for $C_{21}H_{16}Cl_2N_2O_6$: C, 54.44; H, 3.48; N, 6.05. Found: C, 54.41; H, 3.54; N, 6.03.

The E isomer then precipitates to give the E isomer: mp 173–175° C.; IR (KBr) νmax 3399, 3304, 1715, 1556, 1532, 1437, 1350, 1321, 1300, 1242 cm$^{-1}$; $^1$H NMR (DMSO-d$_6$) δ 12.35 (bs, 1 H), 8.25 (s, 1 H), 7.96 (dm, 1 H, J=7.6 Hz), 7.86 (m, 1 H), 7.39 (t, 1 H, J=7.6 Hz), 7.36 (dm, 1 H, J=7.6 Hz), 7.33 (d, 1 H, J=1.7 Hz), 7.14 (d, 1 H, J=1.7 Hz), 4.18 (q, 2 H, J=7.1 Hz), 3.81 (s, 3 H), 1.23 (t, 3 H, J=7.1 Hz). Elemental Analysis Calculated for $C_{21}H_{16}Cl_2N_2O_6$: C, 54.44; H, 3.48; N, 6.05. Found: C, 54.55; H, 3.41; N, 5.93.

EXAMPLE 2
(E) and (Z)-2-(3-Aminophenyl)-3-(2-carboethoxy-4,6-dichloroindol-3-yl)-propenoic acid, methyl ester

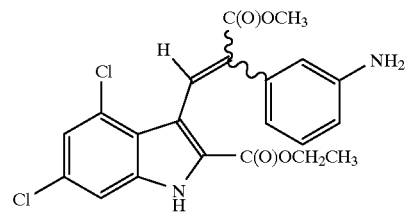

Combine (E) and (Z)-2-(3-nitrophenyl)-3-(2-carboethoxy-4,6-dichloroindol-3-yl)-propenoic acid, methyl ester (16.2 g, 35 mmol) and ethyl acetate (175 mL). Add portionwise tin (II) chloride dihydrate (47.2 g, 209 mmol). Heat to reflux. After 4 hours, cool the reaction mixture to ambient temperature. Slowly add, aqueous saturated sodium bicarbonate solution. Add water and ethyl acetate. Separate the aqueous layer and extract three times with ethyl acetate. Combine the organic layers and extract with aqueous saturated sodium solution. Dry over MgSO$_4$, filter, and evaporate in vacuo to give a residue. Chromatograph the residue on silica gel eluting with ½ ethyl acetate/hexane to give the title compound: mp 249–251° C.; $^1$H NMR (DMSO-d$_6$) δ 12.36 (s, 1 H), 7.45 (d, 1 H, J=1.7 Hz), 7.32 (s, 1 H), 7.22 (d, 1 H, J=1.7 Hz), 7.05 (t, 1 H, J=7.8 Hz), 6.67 (d, 1 H, J=1.9 Hz), 6.55–6.62 (m, 2 H), 5.16 (s, 1 H), 4.27 (q, 2 H, J=7.1 Hz), 3.39 (s, 3 H), 1.25 (t, 3 H, J=7.1). Elemental Analysis Calculated for $C_{21}H_{18}Cl_2N_2O_4 \cdot 2H_2O$: C, 57.09; H, 4.22; N, 6.34. Found: C, 56.94; H, 4.04; N, 6.15.

EXAMPLE 3

(E) and (Z)-2-(3-Acetamidophenyl)-3-(2-carboethoxy-4,6-dichloroindol-3-yl)-propenoic acid, methyl ester

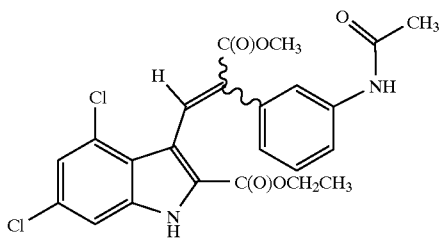

Combine (E) and (Z)-2-(3-aminophenyl)-3-(2-carboethoxy-4,6-dichloroindol-3-yl)-propenoic acid, methyl ester (2.0 g, 4.6 mmol) and triethylamine (1.9 mL, 14 mmol) in dichloromethane (45 mL). Add acetyl chloride (0.82 mL, 12 mmol). After 20 hours, quench with methanol and dilute with dichloromethane. Extract the diluted reaction mixture with brine. Separated the organic layer, dry over $MgSO_4$, filter, and evaporate in vacuo to give the title compound.

EXAMPLE 4

(E) and (Z)-2-(3-Acetamidophenyl)-3-(4,6-dichloroindol-3-yl-2-carboxylic acid)-propenoic acid

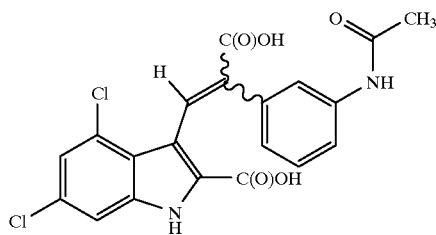

Combine (E) and (Z)-2-(3-acetamidophenyl)-3-(2-carboethoxy-4,6-dichloroindol-3-yl)-propenoic acid, methyl ester (2.39 g, 4.62 mmol) in tetrahydrofuran (25 mL) and water (20 mL). Add lithium hydroxide hydrate (664 mg, 27.7 mmol). Heat to 70° C. After 16 hours, dilute the reaction mixture with water (150 mL) and acidify with 1 M hydrochloric acid. Extract with ethyl acetate and dry the organic layer with $MgSO_4$. Evaporate in vacuo and to give a residue. Slurry the residue in hot ethyl acetate, filter, and dry to give the title compound: mp 270–271° C. (dec); IR (KBr) vmax 3414, 3279, 1688, 1613, 1557, 1242 cm$^{-1}$; $^1$H NMR (DMSO-$d_6$) δ 12.14 (s, 1 H), 9.73 (s,1 H), 8.03 (s, 1 H), 7.39 (dd, 1 H, J=2.0, 7.7 Hz), 7.31 (d, 1 H, J=1.5 Hz), 7.24 (d, 1 H, J=2.0 Hz), 7.13 (d, 1 H, J=1.5 Hz), 6.94 (t, 1 H, J=7.7 Hz), 6.57 (dd, 1 H, J=1.0, 7.7 Hz), 1.94 (s, 3 H). Elemental Analysis Calculated for $C_{20}H_{14}Cl_2N_2O_5$·0.5 HOAc·0.5 ethyl acetate: C, 54.45; H, 3.97; N, 5.52. Found: C, 54.13; H, 3.81; N, 5.76.

EXAMPLE 5

(E) and (Z)-2-(3-Benzamidophenyl)-3-(2-carboethoxy-4,6-dichloroindol-3-yl)-propenoic acid, methyl ester

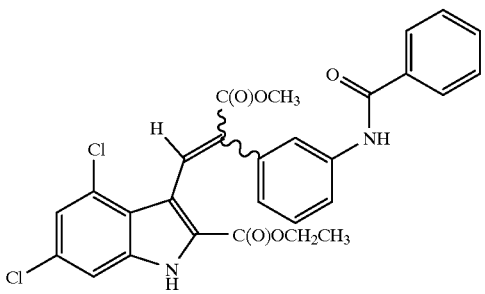

Combine (E) and (Z)-2-(3-aminophenyl)-3-(2-carboethoxy-4,6-dichloroindol-3-yl)-propenoic acid, methyl ester (866 mg, 2.0 mmol), and triethylamine (0.84 mL, 6.0 mmol) in dichloromethane (20 mL). Add benzoyl chloride (0.58 mL, 5.0 mmol). After 20 hours, quench with methanol and dilute with dichloromethane. Extract the diluted reaction mixture with brine. Separated the organic layer dry over $MgSO_4$, filter, and evaporate in vacuo to give the title compound.

EXAMPLE 6

(E) and (Z)-2-(3-Benzamidophenyl)-3-(4,6-dichloroindol-3-yl-2-carboxylic acid)-propenoic acid

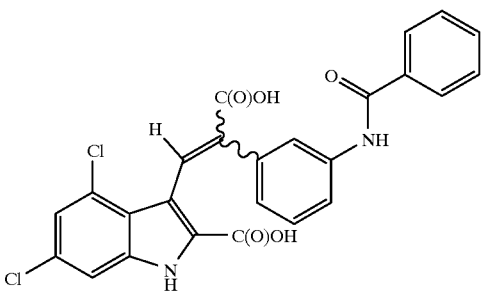

Combine (E) and (Z)-2-(3-benzamidophenyl)-3-(2-carboethoxy-4,6-dichloroindol-3-yl)-propenoic acid, methyl ester (920 mg, 1.43 mmol) in tetrahydrofuran (12 mL) and water (8 mL). Add lithium hydroxide hydrate (205 mg, 8.58 mmol). Heat to 70° C. After 16 hours, dilute the reaction mixture with water (150 mL) and acidify with 1 M hydrochloric acid. Extract with ethyl acetate, dry the organic layer with $MgSO_4$, and evaporate in vacuo and to give a residue. Recrystallization the residue from ethyl acetate/hexane to give the title compound: mp 237–238° C. (dec); IR (KBr) vmax 3420, 3275, 1686, 1611, 1537, 1234, 1225 cm$^{-1}$; $^1$H NMR (DMSO-$d_6$) δ 12.16 (s, 1 H), 10.07 (s,1 H), 8.06 (s, 1 H), 7.95-7.85 (m, 2 H), 7.60-7.45 (m, 4 H), 7.31 (d, 1 H, J=1.8 Hz), 7.13 (d, 1 H, J=1.8 Hz), 6.94 (t, 1 H, J=7.7), 6.65 (dd, 1 H, J=1.0, 7.7 Hz).

EXAMPLE 7

(E) and (Z)-2-(3-(N-Carbomethyloxyamino)phenyl)-3-(2-carboethoxy-4,6-dichloroindol-3-yl)-propenoic acid, methyl ester

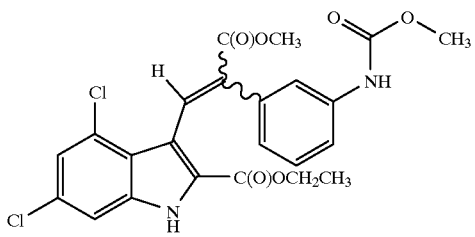

Combine (E) and (Z)-2-(3-aminophenyl)-3-(2-carboethoxy-4,6-dichloroindol-3-yl)-propenoic acid, methyl ester (1.19 g, 2.74 mmol), and pyridine (0.27 mL, 3.3 mmol) in dichloromethane (10 mL). Add methyl chloroformate (0.25 mL, 3.3 mmol). After 20 hours, quench with water and dilute with dichloromethane. Extract the diluted reaction mixture twice with dichloromethane. Combine the organic layers, extract with water, dry over $MgSO_4$, filter, and evaporate in vacuo to give a residue. Recrystallize the residue from dichloromethane, filter, retain the mother liquors, and dry to give the E-isomer: mp 192–194° C.; IR (KBr) vmax 3293, 1742, 1705, 1611, 1553, 1441, 1321, 1300, 1285, 1240 cm$^{-1}$; $^1$H NMR (CDCl$_3$) δ 10.61 (bs, 1 H), 8.16 (s, 1 H), 7.25 (d, 1 H, J=1.7 Hz), 7.19 (bs, 1 H), 7.04 (bs, 1 H), 7.01 (d, 1 H, J=1.7 Hz), 6.93 (t, 1 H, J=1.7 Hz), 6.64 (d, 1 H, J=7.6 Hz), 4.21 (q, 2 H, J=7.1 Hz), 3.79 (s, 3 H), 3.64 (s, 3 H), 2.19 (bs, 1 H), 1.28 (t, 3 H, J=7.1 Hz). Elemental Analysis Calculated for $C_{23}H_{20}Cl_2N_2O_6$: C, 56.23; H, 4.10; N, 5.70. Found: C, 56.12; H, 4.08; N, 5.67.

Evaporate the retained mother liquors and chromatograph on silica gel eluting with cyclohexane/ethyl acetate, 2/1 to give the title compound: mp 87–92° C.; IR (KBr) vmax 3337, 1705, 1611, 1555, 1545, 1443, 1319, 1300, 1283, 1238 cm$^{-1}$; $^1$H NMR (CDCl$_3$) δ 9.34 (bs, 1 H), 9.15 (bs, 1 H), 8.20 (s, 1 H), 7.53 (bt, 1 H, J=1.7 Hz), 7.44 (m, 1 H), 7.43 (s, 1 H), 7.34 (t, 1 H, J=8.0 Hz), 7.21 (dt, 1 H, J=7.6, 1.4 Hz), 7.18 and 7.16 (2d, 3 H, J=1.7 Hz), 7.10 (d, 2 H, J=1.7 Hz), 7.08 (bt, 1 H, J=1.7 Hz), 7.00 (t, 1 H, J=8.0 Hz), 6.76 (bs, 1 H), 6.73 (dt, 1 H, J=7.7, 1.3 Hz), 6.50 (bs, 1 H), 4.33 (q, 2 H, J=7.1 Hz), 4.28 (q, 2 H, J=7,1 Hz), 3.85 (s, 3 H), 3.79 (s, 3 H), 3.68 (s, 3 H), 3.56 (bs, 3 H), 1.34 (t, 3 H, J=7.1 Hz), 1.31 (t, 3 H, J=7.1 Hz).

EXAMPLE 8

(E) and (Z)-2-(3-(N-Carbomethyloxyamino)phenyl)-3-(4,6-dichloroindol-3-yl-2-carboxylic acid)-propenoic acid

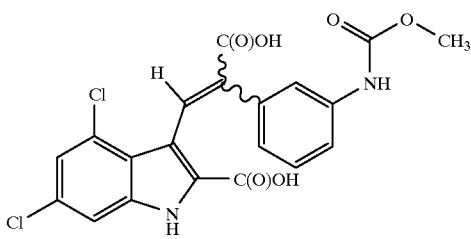

Combine (E) and (Z)-2-(3-(N-carbomethyloxyamino)phenyl)-3-(2-carboethoxy-4,6-dichloroindol-3-yl)-propenoic acid, methyl ester (1.11 g, 2.26 mmol) in tetrahydrofuran (24 mL) and water (16 mL). Add lithium hydroxide hydrate (410 mg, 17.2 mmol). Heat to 70° C. After 16 hours, dilute the reaction mixture with water (150 mL) and acidify with 1 M hydrochloric acid. Extract with ethyl acetate, dry the organic layer with $MgSO_4$, and evaporate in vacuo and to give a residue. Chromatograph the residue on silica gel eluting with dichloromethane/acetic acid, 9/1 to give a second residue. Recrystallize the second residue from ethyl acetate/cyclohexane to give the title compound; mp 250° C. (dec); IR (KBr) vmax 3372, 3081, 1688, 1609, 1589, 1539, 1443, 1294, 1240, 1175 cm$^{-1}$; $^1$H NMR (DMSO-d$_6$) δ 12.86 (bs, 2 H), 12.10 (s, 1 H), 9.43 (s, 1 H), 8.05 (s, 1 H), 7.32 (d, 1 H, J=1.8 Hz), 7.2 (m, 2 H), 7.12 (d, 1 H, J=1.8 Hz), 6.96 (t, 1 H, J=7.9 Hz), 6.59 (dt, 1 H, J=7.7, 1.3 Hz), 3.59 (s, 3 H).

EXAMPLE 9

(E) and (Z)-2-(3-Methylsulfonylamidophenyl)-3-(2-carboethoxy-4,6-dichloroindol-3-yl)-propenoic acid, methyl ester

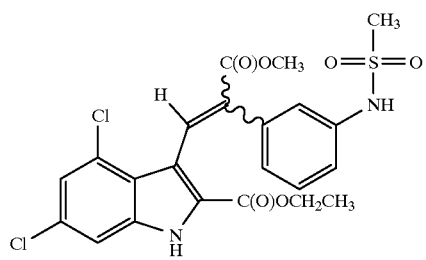

Combine (E) and (Z)-2-(3-aminophenyl)-3-(2-carboethoxy-4,6-dichloroindol-3-yl)-propenoic acid, methyl ester (1.12 g, 2.58 mmol) and pyridine (0.25 mL, 3.1 mmol) in dichloromethane (10 ml). Cool to 0° C. using an ice bath. Add methanesulfonyl chloride (0.24 mL, 3.1 mmol). After 90 minutes, dilute with water and dichloromethane. Separate the organic layer, extract with water, dried over $MgSO_4$, and evaporate in vacuo to give a residue. Chromatograph the residue on silica gel eluting with dichloromethane/ethyl acetate, 7/1, to give the title compound: IR (KBr) vmax 3410, 3297, 1703, 1609, 1437, 1321, 1240, 1152, 980 cm$^{-1}$; $^1$H NMR (CDCl$_3$) δ E-isomer: 9.37 (bs, 1 H), 8.24 (s, 1 H), 7.22 (d, 1 H, J=1.7 Hz), 7.07 (d, 1 H, J=1.7 Hz), 7.0-6.9 (m, 4 H), 6.65 (bs, 1 H), 4.31 (q, 2 H, J=7.2 Hz), 3.87 (s, 3 H), 2.60 (s, 3 H), 1.36 (t, 3 H, J=7.2 Hz); Z-isomer: 9.32 (bs, 1 H), 7.48 (s, 1 H), 7.4-7.3 (m, 4 H), 7.25 (d, 1 H, J=1.7 Hz), 7.12 (d, 1 H, J=1.7 Hz), 7.10 (m, 1 H), 4.35 (q, 2 H, J=7.2 Hz), 3.53 (s, 3 H), 3.06 (s, 3 H), 1.32 (t, 3 H, J=7.2 Hz).

EXAMPLE 10

(E) and (Z)-2-(3-Methylsulfonylamidophenyl)-3-(4,6-dichloroindol-3-yl-2-carboxylic acid)-propenoic acid

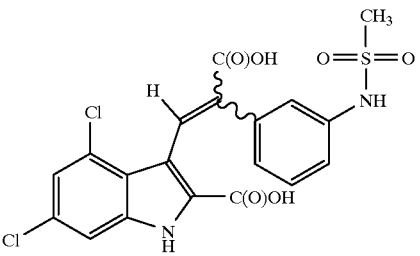

Prepare by the method of Example 4 using (E) and (Z)-2-(3-methylsulfonylamidophenyl)-3-(2-carboethoxy-4,6-dichloroindol-3-yl)-propenoic acid, methyl ester (1.17 g, 2.29 mmol) to give the title compound: mp >270° C.; IR (KBr) vmax 3418, 3300, 3200, 3094, 1686, 1615, 1319, 1306, 1240, 1140, 980 cm$^{-1}$; $^1$H NMR (DMSO-d$_6$) δ 12.93 (bs, 2 H), 12.18 (s, 1 H), 9.44 (s, 1 H), 8.07 (s, 1 H), 7.32 (d, 1 H, J=1.7 Hz), 7.13 (d, 1 H, J=1.7 Hz), 7.08 (dt, 1 H, J=7.7, 0.7 Hz), 6.9 (m, 2 H), 6.80 (dm, 1 H, J=7.7 Hz), 2.48 (s, 3 H). Elemental Analysis Calculated for C$_{19}$H$_{14}$Cl$_2$N$_2$O$_6$S: C, 48.63; H, 3.01; N, 5.97. Found: C, 48.67; H, 3.18; N, 5.71.

EXAMPLE 11

(E) and (Z)-2-(3-(N-Carboethyloxyamino)phenyl)-3-(2-carboethoxy-4,6-dichloroindol-3-yl)-propenoic acid, methyl ester

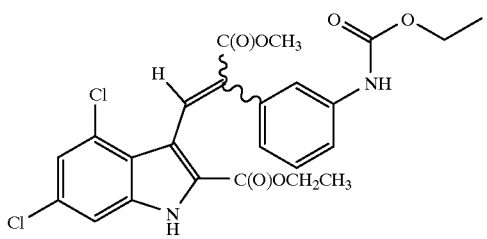

Prepare by the method of Example 7 using (E) and (Z)-2-(3-aminophenyl)-3-(2-carboethoxy-4,6-dichloroindol-3-yl)-propenoic acid, methyl ester and ethyl chloroformate to give the title compound. MS (CI/NH$_3$) M+NH$_4$$^+$/e 522. Elemental Analysis Calculated for C$_{24}$H$_{22}$Cl$_2$N$_2$O$_6$: C, 57.04; H, 4.39; N, 5.54. Found: C, 56.86; H, 4.35; N, 5.25.

EXAMPLE 12

(E) and (Z)-2-(3-(N-Carboethyloxyamino)phenyl)-3-(4,6-dichloroindol-3-yl-2-carboxylic acid)-propenoic acid

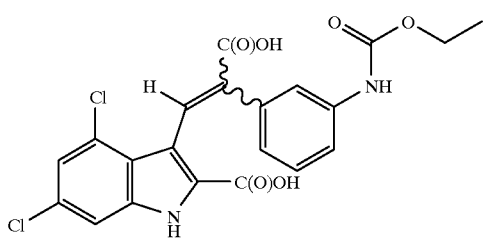

Prepare by the method of Example 8 using (E) and (Z)-2-(3-(N-carboethyloxyamino)phenyl)-3-(2-carboethoxy-4,6-dichloroindol-3-yl)-propenoic acid to give the title compound. MS (CI/NH$_3$) M+NH$_4$$^+$/e 480.

EXAMPLE 13

(E) and (Z)-2-(3-(N-Carboisopropyloxyamino)phenyl)-3-(2-carboethoxy-4,6-dichloroindol-3-yl)-propenoic acid, methyl ester

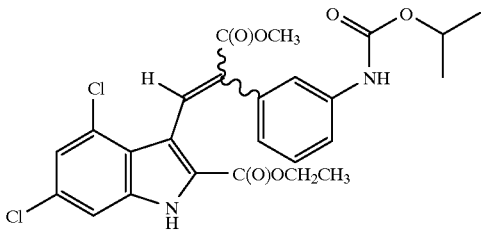

prepare by the method of Example 7 using (E) and (Z)-2-(3-aminophenyl)-3-(2-carboethoxy-4,6-dichloroindol-3-yl)-propenoic acid, methyl ester and isopropyl chloroformate to give the title compound. MS (CI/NH$_3$) M+NH$_4$$^+$/e 536. Elemental Analysis Calculated for C$_{25}$H$_{24}$Cl$_2$N$_2$O$_6$: C, 57.81; H, 4.66; N, 5.39. Found: C, 58.14; H, 4.76; N, 5.33.

EXAMPLE 14

(E) and (Z)-2-(3-(N-Carboisopropyloxyamino)phenyl)-3-(4,6-dichloroindol-3-yl-2-carboxylic acid)-propenoic acid

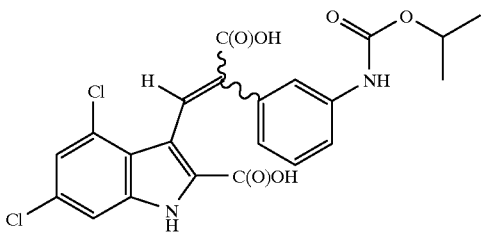

prepare by the method of Example 8 (E) and (Z)-2-(3-(N-carboisopropyloxyamino)phenyl)-3-(2-carboethoxy-4,6-dichloroindol-3-yl)-propenoic acid, methyl ester to give the title compound. MS (CI/NH$_3$) M+NH$_4$$^+$/e 494,496.

EXAMPLE 15

(E) and (Z)-2-(3-Benzenesulfonylamidophenyl)-3-(2-carboethoxy-4,6-dichloroindol-3-yl)-propenoic acid, methyl ester

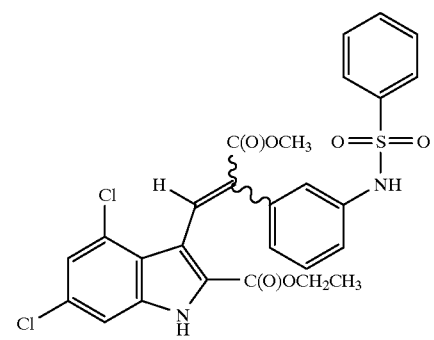

Prepare by the method of Example 9 using (E) and (Z)-2-(3-aminophenyl)-3-(2-carboethoxy-4,6-dichloroindol-3-yl)-propenoic acid, methyl ester and benzenesulfonyl chloride to give the title compound.

EXAMPLE 16
(E) and (Z)-2-(3-Benzenesulfonylamidophenyl)-3-(4,6-dichloroindol-3-yl-2-carboxylic acid)-propenoic acid

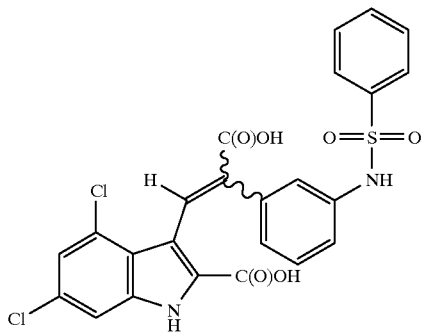

Prepare by the method of Example 4 using (E) and (Z)-2-(3-benzenesulfonylamidophenyl)-3-(2-carboethoxy-4,6-dichloroindol-3-yl)-propenoic acid, methyl ester to give the title compound.

EXAMPLE 17
(E) and (Z)-2-(4-Nitrophenyl)-3-(2-carboethoxy-4,6-dichloroindol-3-yl)-propenonitrile

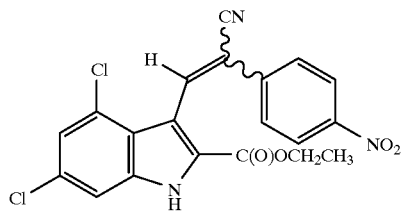

Combine 3-formyl-2-carboethoxy-4,6-dichloroindole (5.0 g, 17.48 mmol), 4-nitrophenylacetonitrile (2.83 g, 17.48 mmol), piperidine (0.2 mL), and ethanol (50 mL). Heat to reflux. After 16 hours, cool to ambient temperature. Cool to 0° C. to give a solid. Filter and dry to give the title compound: IR (KBr) vmax 3402, 3283, 2224, 1709, 1684, 1609, 1522, 1344, 1238 cm$^{-1}$; $^1$H NMR (DMSO-d$_6$) δ 12.92 (s, 1 H), 8.65 (s, 1 H), 8.36 (d, 1 H, J=8.9 Hz), 8.03 (d, 1 H, J=8.9 Hz), 7.53 (d, 1 H, J=1.6 Hz), 7.37 (d, 1 H, J=1.6 Hz), 4.34 (q, 2 H, J=7.1 Hz), 1.24 (t, 3 H, J=7.1). Elemental Analysis Calculated for C$_{20}$H$_{13}$Cl$_2$N$_3$O$_4$: C, 55.83; H, 3.05; N, 9.77. Found: C, 55.65; H, 2.70; N, 9.67.

EXAMPLE 18
(E) and (Z)-2-(4-Aminophenyl)-3-(2-carboethoxy-4,6-dichloroindol-3-yl)-propenonitrile

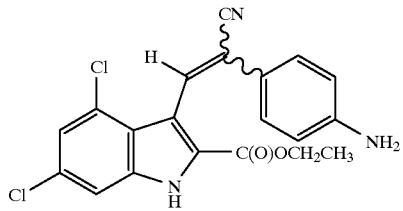

Combine (E) and (Z)-2-(4-nitrophenyl)-3-(2-carboethoxy-4,6-dichloroindol-3-yl)-propenonitrile (6.93 g, 16.1 mmol) and ethanol (50 mL). Add portionwise tin (II) chloride dihydrate (18.2 g, 80.5 mmol). Heat to 70° C. After 4 hours, cool the reaction mixture to ambient temperature. Evaporate in vacuo. Add water and slowly add, aqueous saturated sodium bicarbonate solution until the pH is about 7.5. Extract 2 times with ethyl acetate. Combine the organic layers and extract with brine. Dry over MgSO$_4$, filter, and evaporate in vacuo to give a residue. Chromatograph the residue on silica gel eluting with 2/1 hexane/ethyl acetate to give the title compound: IR (KBr) vmax 3385, 3302, 2222, 1690, 1622, 1609, 1514, 1238 cm$^{-1}$; $^1$H NMR (DMSO-d$_6$) δ 10.15 (s, 1 H), 7.85 (s, 1 H), 7.52 (d, 1 H, J=7.4 Hz), 7.31 (s, 1 H), 7.14 (d, 1 H, J=1.3 Hz), 6.74 (d, 1 H, J=7.4 Hz), 4.36 (q, 2 H, J=7.1 Hz), 1.27 (t, 3 H, J=7.1). Elemental analysis Calculated for C$_{20}$H$_{15}$Cl$_2$N$_3$O$_2$: C, 60.02; H, 3.78; N, 10.50. Found: C, 59.65; H, 3.48; N, 10.07.

EXAMPLE 19
(E) and (Z)-2-(4-Aminophenyl)-3-(2-carboethoxy-4,6-dichloroindol-3-yl)-propenoic acid amide

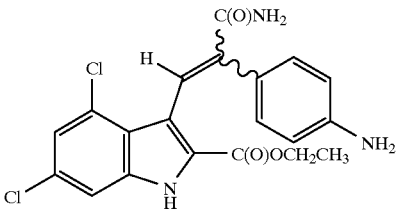

Combine (E) and (Z)-2-(4-aminophenyl)-3-(2-carboethoxy-4,6-dichloroindol-3-yl)-propenonitrile (6.20 g, 15.5 mmol), sulfuric acid (20 mL) and acetic acid (20 mL). Heat to about 70° C. After 3 hours, cool in a ice/water bath to give a solid. Collect by filtration give the title compound: $^1$H NMR (DMSO-d$_6$) δ 12.24-12.20 (s, 1 H), 7.64 (s, 1 H), 7.40 (m, 2 H), 7.2 (s, 2 H), 6.84 (d, 2 H), 6.80 (d, 2 H), 4.20 (q, 2 H), 4.4-3.4 (bs, 2 H), 1.25 (t, 3 H).

EXAMPLE 20
(E) and (Z)-2-(4-(N-Carbomethyloxyamino)phenyl)-3-(2-carboethoxy-4,6-dichloroindol-3-yl)-propenoic acid amide

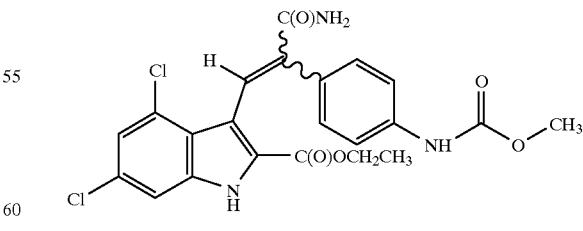

Prepare by the method of Example 7 using (E) and (Z)-2-(4-aminophenyl)-3-(2-carboethoxy-4,6-dichloroindol-3-yl)-propenonitrile to give the title compound.

EXAMPLE 21

(E) and (Z)-2-(4-(N-Carbomethyloxyamino)phenyl)-3-(4,6-dichloroindol-3-yl-2-carboxylic acid)-propenoic acid amide

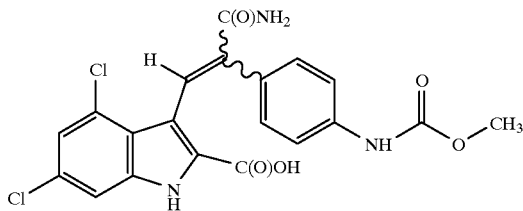

Prepare by the method of Example 8 using (E) and (Z)-2-(4-(N-carbomethyloxyamino)phenyl)-3-(4,6-dichloroindol-3-yl-2-carboxylic acid)-propenoic acid amide to give the title compound.

EXAMPLE 22

(E) and (Z)-2-(4-Aminophenyl)-3-(4,6-dichloroindol-3-yl-2-carboxylic acid)-propenoic acid

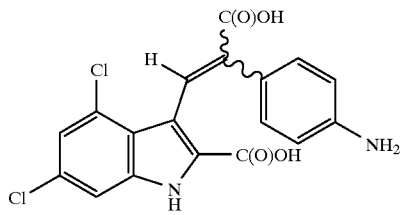

Combine (E) and (Z)-2-(4-aminophenyl)-3-(2-carboethoxy-4,6-dichloroindol-3-yl)-propenoic acid amide (1.90 g, 5.38 mmol) and aqueous 6 M sodium hydroxide solution (20 mL). Heat to 105° C. After 14 hours, cool to 0° C. and acidify to pH 3 with aqueous 6 M hydrochloric acid solution to form a solid. Collect the solid by filtration to give the title compound: IR (KBr) vmax 3395, 3271, 1724, 1612, 1176, 1082 cm$^{-1}$; $^1$H NMR (DMSO-d$_6$) δ 12.12 (s, 1 H), 7.87 (s, 1 H), 7.33 (d, 1 H, J=1.8 Hz), 7.10 (d, 1 H, J=1.8 Hz), 6.62 (d, 2 H, J=8.6 Hz), 6.23 (d, 2 H, J=8.6 Hz).

EXAMPLE 23

(E) and (Z)-2-(4-Aminophenyl)-3-(2-carbomethoxy-4,6-dichloroindol-3-yl)-propenoic acid, methyl ester

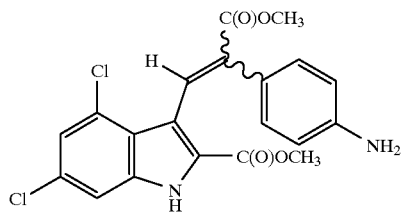

Combine (E) and (Z)-2-(4-aminophenyl)-3-(4,6-dichloroindol-3-yl-2-carboxylic acid)-propenoic acid (10 mmol) and methanol (50 mL). Add sulfuric acid (1 mL). After 24 hours, concentrate in vacuo to about 20 mL. Dilute the reaction mixture with dichloromethane and extract with aqueous saturated sodium carbonate solution. Separate the organic layer, dry over MgSO$_4$, and evaporate in vacuo to give the title compound.

EXAMPLE 24

(E) and (Z)-2-(4-Acetamidophenyl)-3-(2-carbomethoxy-4,6-dichloroindol-3-yl)-propenoic acid, methyl ester

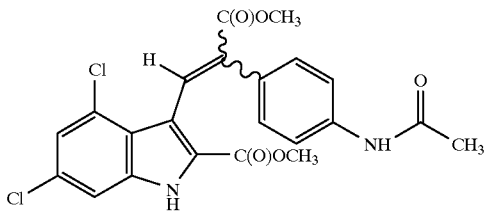

Prepare by the method of Example 3 using (E) and (Z)-2-(4-aminophenyl)-3-(2-carbomethoxy-4,6-dichloroindol-3-yl)-propenoic acid, methyl ester to give the title compound.

EXAMPLE 25

(E) and (Z)-2-(4-Acetamidophenyl)-3-(4,6-dichloroindol-3-yl-2-carboxylic acid)-propenoic acid

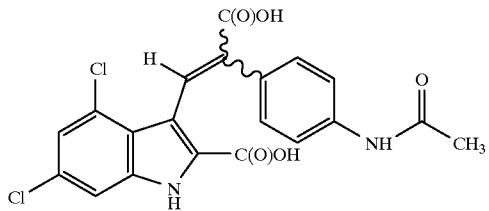

Prepare by the method of Example 4 using (E) and (Z)-2-(4-acetamidophenyl)-3-(2-carbomethoxy-4,6-dichloroindol-3-yl)-propenoic acid, methyl ester to give the title compound.

EXAMPLE 26

(E) and (Z)-2-(4-(N-carbomethyloxyamino)phenyl)-3-(2-carbomethoxy-4,6-dichloroindol-3-yl)-propenoic acid, methyl ester

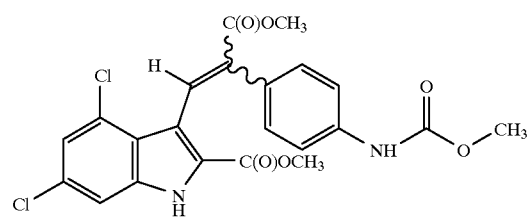

Prepare by the method of Example 7 using (E) and (Z)-2-(4-aminophenyl)-3-(2-carbomethoxy-4,6-dichloroindol-3-yl)-propenoic acid, methyl ester to give the title compound.

EXAMPLE 27
(E) and (Z)-2-(4-(N-Carbomethyloxyamino)phenyl)-3-(4,6-dichloroindol-3-yl-2-carboxylic acid)-propenoic acid

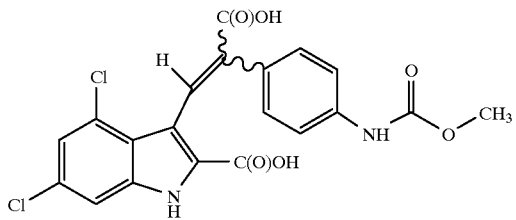

Prepare by the method of Example 8 using (E) and (Z)-2-(4-(N-Carbomethyloxyamino)phenyl)-3-(2-carbomethoxy-4,6-dichloroindol-3-yl)-propenoic acid, methyl ester to give the title compound.

EXAMPLE 28
(E) and (Z)-2-(3-Nitrophenyl)-3-(2-carboethoxy-4,6-dichloroindol-3-yl)-propenonitrile

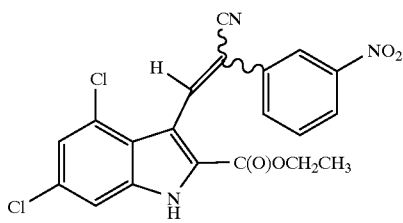

Combine 3-formyl-2-carboethoxy-4,6-dichloroindole (13.95 g, 0.49 mol), 4-nitrophenylacetonitrile (7.9 g, 10.49 mol), piperidine (1.5 mL), and ethanol (500 mL). Heat to reflux. After 4 days, cool to ambient temperature. Cool to 0° C. to give a solid. Filter, rinse with ethanol and methyl t-butyl ether, and dry to give the title compound: $R_f$=0.60 (silica gel, 50% ethyl acetate/heptane). Elemental Analysis Calculated for $C_{20}H_{13}Cl_2N_3O_4$: C, 55.83; H, 3.05; N, 9.77. Found: C, 55.69; H, 3.07; N, 9.66.

EXAMPLE 29
(E) and (Z)-2-(3-Aminophenyl)-3-(2-carboethoxy-4,6-dichloroindol-3-yl)-propenonitrile

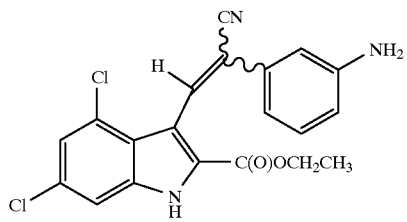

Combine (E) and (Z)-2-(3-nitrophenyl)-3-(2-carboethoxy-4,6-dichloroindol-3-yl)-propenonitrile (2.58 g, 0.042 mmol), tin (II) chloride dihydrate (6.8 g, 0.21 mmol) in ethyl acetate (120 mL). Heat to reflux. After 3 hours, cool the reaction mixture to ambient temperature. Slowly add aqueous saturated sodium bicarbonate solution (150 mL). Add water (300 mL). Extract twice with ethyl acetate. Combine the organic layers, dry over $MgSO_4$, filter, and evaporate in vacuo to give the title compound: $R_f$=0.45 (silica gel, 50% ethyl acetate/heptane). Elemental analysis Calculated for $C_{20}H_{15}Cl_2N_3O_2$: C, 60.02; H, 3.78; N, 10.50. Found: C, 59.70; H, 3.78; N, 10.20.

EXAMPLE 30
(E) and (Z)-2-(3-Aminophenyl)-3-(2-carboethoxy-4,6-dichloroindol-3-yl)-propenoic acid amide

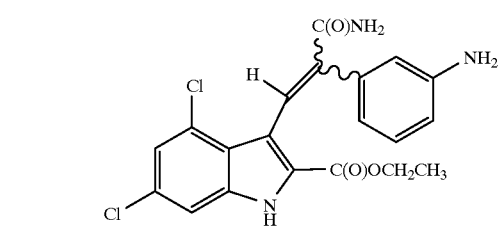

Combine (E) and (Z)-2-(3-aminophenyl)-3-(2-carboethoxy-4,6-dichloroindol-3-yl)-propenonitrile (7.88 g, 0.020 mmol), sulfuric acid (25 mL) and acetic acid (25 mL). Heat to about 90° C. After 2 hours, cool the reaction mixture and slowly adjust the pH to 5 using 6 M aqueous sodium hydroxide solution. Cool to 0° C. to give a solid. After 1 hour, collect by filtration. Combine the solid and ethyl acetate (1 L) and heat to reflux. After 1 hour, cool, filter, and extract with water. Dry the organic layer over $MgSO_4$, filter, and evaporate in vacuo to give the title compound.

EXAMPLE 31
(E) and (Z)-2-(3-(N-Carbomethyloxyamino)phenyl)-3-(2-carboethoxy-4,6-dichloroindol-3-yl)-propenoic acid amide

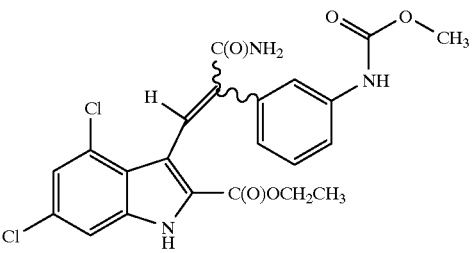

Prepare by the method of Example 7 using (E) and (Z)-2-(3-aminophenyl)-3-(2-carboethoxy-4,6-dichloroindol-3-yl)-propenonitrile to give the title compound.

EXAMPLE 32
(E) and (Z)-2-(3-(N-Carbomethyloxyamino)phenyl)-3-(4,6-dichloroindol-3-yl-2-carboxylic acid)-propenoic acid amide

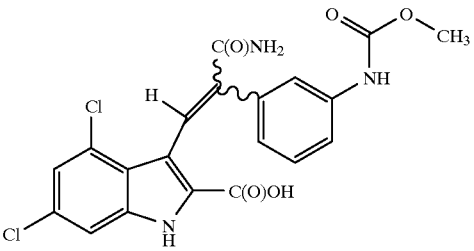

Prepare by the method of Example 8 using (E) and (Z)-2-(3-(N-carbomethyloxyamino)phenyl)-3-(2-carboethoxy-4,6-dichloroindol-3-yl)-propenoic acid amide to give the title compound.

EXAMPLE 33

(E) and (Z)-2-(3-Acetamidophenyl)-3-(2-carboethoxy-4,6-dichloroindol-3-yl)-propenoic acid amide

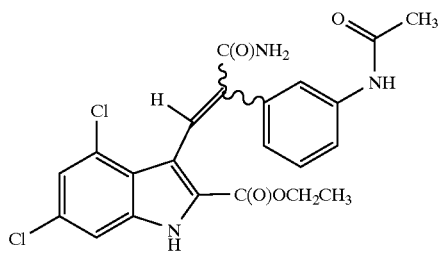

Prepare by the method of Example 3 using (E) and (Z)-2-(3-aminophenyl)-3-(2-carboethoxy-4,6-dichloroindol-3-yl)-propenonitrile to give the title compound.

EXAMPLE 34

(E) and (Z)-2-(3-Acetamidophenyl)-3-(4,6-dichloroindol-3-yl-2-carboxylic acid)-propenoic acid amide

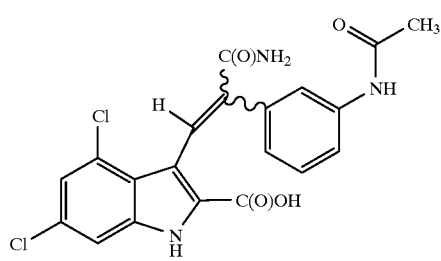

Prepare by the method of Example 4 using (E) and (Z)-2-(3-acetamidophenyl)-3-(2-carboethoxy-4,6-dichloroindol-3-yl)-propenoic acid amide to give the title compound.

PREPARATION 3

3-Methoxy-2-(2-nitrophenyl)-propenoic acid, methyl ester

Prepare by the method of Preparation 2 using (2-nitrophenyl)acetic acid to give the title compound.

EXAMPLE 35

(E) and (Z)-2-(2-Nitrophenyl)-3-(2-carboethoxy-4,6-dichloroindol-3-yl)-propenoic acid, methyl ester

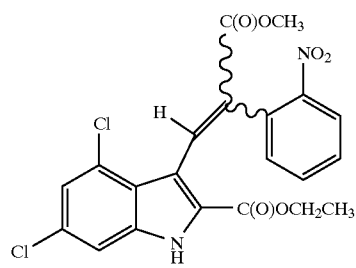

Prepare by the method of Example 1 using 3-methoxy-2-(2-nitrophenyl)-propenoic acid, methyl ester to give the title compound.

EXAMPLE 36

(E) and (Z)-2-(2-Aminophenyl)-3-(2-carboethoxy-4,6-dichloroindol-3-yl)-propenoic acid, methyl ester

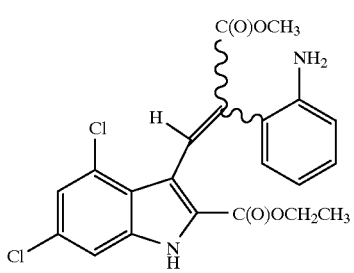

Prepare by the method of Example 2 using (E) and (Z)-2-(2-nitrophenyl)-3-(2-carboethoxy-4,6-dichloroindol-3-yl)-propenoic acid, methyl ester to give the title compound.

EXAMPLE 37

(E) and (Z)-2-(2-Acetamidophenyl)-3-(2-carboethoxy-4,6-dichloroindol-3-yl)-propenoic acid, methyl ester

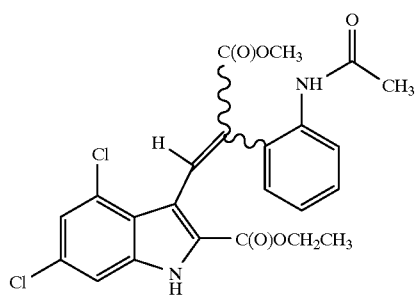

Prepare by the method of Example 3 using (E) and (Z)-2-(2-aminophenyl)-3-(2-carboethoxy-4,6-dichloroindol-3-yl)-propenoic acid, methyl ester to give the title compound.

EXAMPLE 38

(E) and (Z)-2-(2-Acetamidophenyl)-3-(4,6-dichloroindol-3-yl-2-carboxylic acid)-propenoic acid

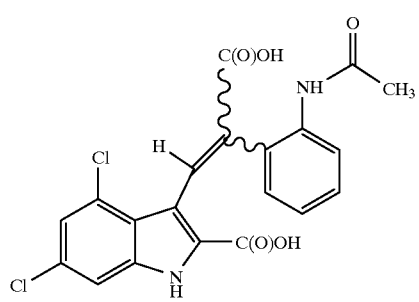

Prepare by the method of Example 4 using (E) and (Z)-2-(2-acetamidophenyl)-3-(2-carboethoxy-4,6-dichloroindol-3-yl)-propenoic acid, methyl ester to give the title compound.

EXAMPLE 39

(E) and (Z)-2-(3-(Formamidophenyl)-3-(2-carboethoxy-4,6-dichloroindol-3-yl)-propenoic acid, methyl ester

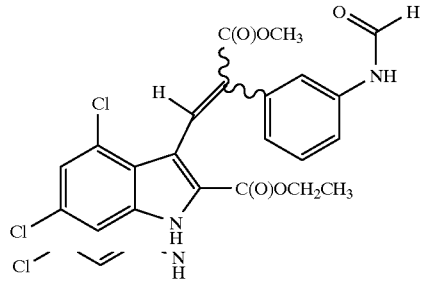

Combine (E) and (Z)-2-(3-aminophenyl)-3-(2-carboethoxy-4,6-dichloroindol-3-yl)-propenoic acid, methyl ester (5.45 g, 12.6 mmol) and ethyl formate (800 mL). After 20 hours, evaporate in vacuo to give a residue. Dilute the residue with ethyl acetate and extract with brine. Separate the organic layer, dry over $MgSO_4$, filter, and evaporate in vacuo to give the title compound.

EXAMPLE 40

(E) and (Z)-2-(3-(N-Methylacetamidophenyl)-3-(2-carboethoxy-4,6-dichloroindol-3-yl)-propenoic acid, methyl ester

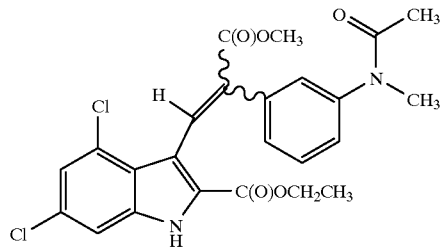

Combine (E) and (Z)-2-(3-(formamidophenyl)-3-(2-carboethoxy-4,6-dichloroindol-3-yl)-propenoic acid, methyl ester (5.5 g, 12 mmol) and tetrahydrofuran (30 mL). Add a solution of borane dimethylsulfide complex in tetrahydrofuran (15 mL, 2 M, 30 mmol). Heat to 60° C. After 15 minutes, cool to ambient temperature and carefully quench with methanol. Evaporate in vacuo to give a residue. Chromatograph the residue on silica gel eluting with 30% ethyl acetate/cyclohexane to give (E) and (Z)-2-(3-(N-methylaminophenyl)-3-(2-carboethoxy-4,6-dichloroindol-3-yl)-propenoic acid, methyl ester. MS (CI/$CH_4$) M+$C_2H_5^+$/e 457,477.

Combine (E) and (Z)-2-(3-(N-methylaminophenyl)-3-(2-carboethoxy-4,6-dichloroindol-3-yl)-propenoic acid, methyl ester (4.6 mmol) and triethylamine (1.9 mL, 14 mmol) in dichloromethane (45 mL). Add acetyl chloride (0.82 mL, 12 mmol). After 20 hours, quench with methanol and dilute with dichloromethane. Extract the diluted reaction mixture with brine. Separated the organic layer, dry over $MgSO_4$, filter, and evaporate in vacuo to give the title compound.

EXAMPLE 41

(E) and (Z)-2-(3-(N-Methylacetamidophenyl)-3-(4,6-dichloroindol-3-yl-2-carboxylic acid)-propenoic acid

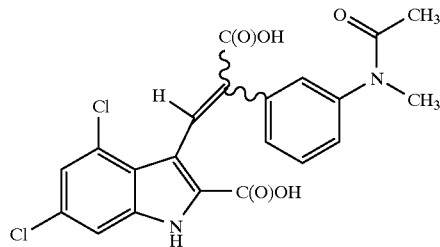

Prepare by the method of Example 4 using (E) and (Z)-2-(3-(N-methylacetamidophenyl)-3-(2-carboethoxy-4,6-dichloroindol-3-yl)-propenoic acid, methyl ester to give the title compound.

EXAMPLE 42

(E) and (Z)-2-(3-(N-Methyl-N-carbomethyloxyaminophenyl)-3-(2-carboethoxy-4,6-dichloroindol-3-yl)-propenoic acid, methyl ester

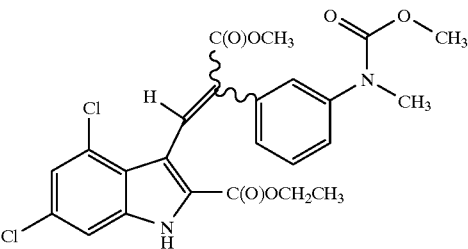

Prepare by the method of Example 7 using(E) and (Z)-2-(3-(N-methylaminophenyl)-3-(2-carboethoxy-4,6-dichloroindol-3-yl)-propenoic acid, methyl ester to give the title compound.

EXAMPLE 43

(E) and (Z)-2-(3-(N-Methylacetamidophenyl)-3-(4,6-dichloroindol-3-yl-2-carboxylic acid)-propenoic acid

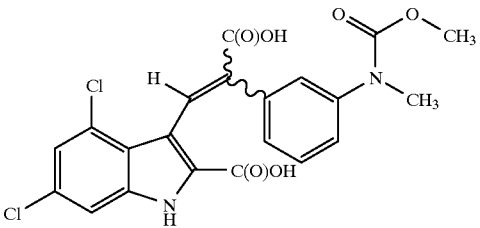

Prepare by the method of Example 8 using (E) and (Z)-2-(3-(N-methyl-N-carbomethyloxyaminophenyl)-3-(2-carboethoxy-4,6-dichloroindol-3-yl)-propenoic acid, methyl ester to give the title compound.

The compounds of formula (1) are excitatory amino acid antagonists. They antagonize the effects which excitatory amino acids have upon the NMDA receptor complex. They preferentially bind to the strychnine-insensitive glycine binding site on the NMDA receptor complex associated with the treatment of a number of disease states. See Palfreyman, M. G. and B. M. Baron, *Excitatory Amino Acid Antagonists*, B. S. Meldrum ed., Blackwell Scientific, 101–129 (1991);

and, J. A. Kemp and P. D. Leeson, *Trends in Pharmacological Sciences*, 14, 20–25 (1993), A. J. Carter, *Drugs of the Future*, 17, 595–613 (1992); and P. D. Leeson and L. L. Iverson, *J. Med. Chem.*, 37, 4053–4067 (1994).

Affinity for brain strychnine-insensitive glycine binding site on the NMDA receptor complex can be determined in the following way. Approximately 50 to 60 young male Sprague-Dawley rats (C-D strain), are sacrificed by decapitation and their cerebral cortices and hippocampi are removed. The two brain regions are combined and homogenized in 15 volumes of ice-cold 0.32 M sucrose using a teflon glass homogenizer (10 passes at 400 rpm). The homogenates are centrifuged at 1000×gravity for 10 minutes and the supernatants are transferred and recentrifuged at 44,000×gravity for 20 minutes. The upper white part of the pellets are resuspended with a pipet in ice-cold water and homogenized with a polytron (setting 6 for 10 seconds) and centrifuged at 44,000×gravity for 15 minutes. Pellets are then resuspended in 6 volumes of water and placed in a dry-ice/methanol bath until frozen, followed by thawing at 37° C. in a shaking water bath. The freeze/thaw process is repeated and final volumes of the suspensions adjusted to 15 volumes with water and centrifuged at 44,000×gravity for 15 minutes. The resulting pellets are resuspended in 15 volumes of 10 mM HEPES-KOH (N-2-hydroxyethyl-piperazine-N'-2-ethanesulsonic acid—potassium hydroxide) at pH 7.4 containing 0.04% Triton X-100 (v/v), incubated at 37° C. for 15 minutes and centrifuged at 44,000×gravity for 15 minutes. The pellets are then resuspended in 15 volumes of 10 mM HEPES-KOH at pH 7.4 with a polytron (setting of 6 for 10 seconds) and centrifuged at 44,000×gravity for 15 minutes. Repeat this resuspension/centrifugation process an additional 2 times. The membranes are then resuspended in 3 volumes of 10 mM HEPES and stored frozen at –80° C.

When the assay is to be performed, the membranes are thawed at ambient temperature and diluted with 9 volumes of 10 mM HEPES-KOH pH 7.4 and incubated at 25° C. for 15 minutes This is followed by centrifugation at 44,000× gravity for 15 minutes then resuspension with 10 mM HEPES-KOH at pH 7.4 using a polytron. The incubation/resuspension/centrifugation process is repeated an additional 2 times and the final pellet is resuspended in 6 volumes of 50 mM HEPES-KOH at pH 7.4. Incubation vials in triplicate, receive 50 μL of 200 nM [$^3$H]-glycine, 50 μL of 1000 nM strychnine, 50 μL of various concentrations of test compounds diluted with 50 mM HEPES-KOH at pH 7.4, and 200 μL of membrane suspension (400 μg protein/aliquot) in a final volume of 0.5 mL. Incubations are carried out at 4° C. for 30 minutes and are terminated by centrifugation at 46,000×gravity for 10 minutes. The supernatants are decanted and the pellets are rinsed rapidly with 2 mL of ice-cold 50 mM HEPES-KOH at pH 7.4, then dissolved in 4 mL of Ready Protein (Beckman Instruments) and counted by liquid scintillation spectrometry.

Specific binding of [$^3$H]-glycine is measured as the total radioactivity bound minus that bound to the receptors in the presence of 0.1 mM M D-serine. Total membrane-bound radioactivity is less that 2% of that added to the assay vials. Since these conditions limit the total binding to less than 10% of the radioactivity, the concentration of free ligand does not change appreciably during the assay. The results of this assay are expressed as an $IC_{50}$, that is the molar concentration of a compound which causes 50% inhibition of ligand binding.

The compounds exhibit anticonvulsant properties and are useful in the treatment of convulsive disorders, such as grand mal seizures, petit mal seizures, psychomotor seizures, autonomic seizures, etc. One method of demonstrating their antiepileptic properties is by their ability to inhibit the seizures that are caused by the administration of quinolinic acid. This test can be conducted in the following manner.

One group containing ten mice are administered 0.01–100 micrograms of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of tonic seizures. The control group will have a statistically higher rate of tonic seizures than will the test group.

Another method of demonstrating the antiepileptic properties of these compounds is by their ability to inhibit audiogenic convulsions in DBA/2J mice. This test can be conducted in the following manner. Typically one group of from 6–8 male DBA/2J audiogenic mice are administered from about 0.01 micrograms to about 10 micrograms of the test compound into the lateral ventricle of the brain or from about 0.1 milligrams to about 300 milligrams intraperitoneally. A second group of mice are administered an equal volume of a saline control by the same route. Five minutes to 4 hours later, the mice are placed individually in glass jars and are exposed to a sound of 110 decibels for 30 seconds. Each mouse is observed during the sound exposure for signs of seizure activity. The control group will have a statistically higher incidence of seizures than the group which receives the test compound.

The compounds of formula (1) are useful for preventing or minimizing the damage which nervous tissues contained within the central nervous system (CNS) suffer upon exposure to either ischemic, traumatic, or hypoglycemic conditions including strokes or cerebrovascular accidents, cardiovascular surgery, concussions, hyperinsulinemia, cardiac arrest, drownings, suffocations, and neonatal anoxic trauma. The compounds should be administered to the patient within 24 hours of the onset of the hypoxic, ischemic, traumatic, or hypoglycemic condition in order to minimize the CNS damage which the patient will experience.

The compounds of formula (1) minimize or prevent CNS damage after ischemia. These anti-ischemia properties can be demonstrated by the ability of the compounds of formula (1) to reduce infarct volume in rats subjected to middle cerebral artery occlusion as follows. Male Sprague-Dawley rats are subjected to occlusion of the middle cerebral artery by an adaptation of the method of H. Memezawa et al., *Ischemia Penumbra in a Model of Reversible Middle Cerebral Artery Occlusion in the Rat, Experimental Brain Research*, 89, 67–78 (1992). The rat is anesthetized with halothane in a mixture of $O_2$ and NO (1:2 ratio) and a midline incision is made in the ventral neck region. An indwelling venous catheter is placed in the jugular vein. Under a dissecting microscope, the left common carotid artery is identified at its bifurcation into the external carotid artery and internal carotid artery. Two ties are placed on the external carotid artery. The internal carotid artery is exposed distally to the point of its bifurcation into the intracranial internal carotid artery and the pterygopalatine artery. A small cut is made in the distal segment of the external carotid artery and a 3-0 nylon monofilament is introduced into the lumen of the external carotid artery. The two previously placed ties are tightened around the monofilament. The external carotid artery is cut and reflected caudally so that the monofilament can be advanced into the internal carotid artery, past the distal internal carotid artery/pterygopalatine artery bifurcation and continuing into the intranial segment of the internal carotid artery to a distance of 20 mm, at which point the origin of the middle cerebral artery is occluded. The ties are then tightened and the wound is closed. Compound or vehicle alone is administered intravenously at a pre-determined time post-ischemia and dosing can be single, multiple, or by continuous infusion.

Animals are given food and water and allowed to survive for 24 h. Prior to sacrifice, the rat is weighed and given a battery of four neurological tests to measure muscle strength, grooming skills, postural reflexes and sensorimotor integration, as described by C. G. Markgraf et al., *Sensorimotor and Cognitive Consequences of Middle Cerebral Artery Occlusion in Rats, Brain Research*, 575, 238–246 (1992). The animal is then decapitated, the brain is removed, sliced into six sections and incubated in 2% 2,3,5-triphenyltetrazolium chloride for 30 minutes, as described by K. Isayama et al., *Evaluation of 2,3,5-Triphenyltetrazolium Chloride Stains to Delineate Rat Brain Infarcts, Stroke* 22, 1394–1398 (1991). The area of infarction is clearly visible. Infarct area is determined by computer-assisted image analysis for each of the six sections and integrated over the anterior-posterior extent of the brain to yield infarct volume. Group means±SE are determined for infarct volume and for the four behavioral tests and compared for the groups using ANOVA with orthogonal contrasts.

Another method of demonstrating the ability of the compounds of formula (1) minimize or prevent CNS damage after ischemia is as follows: An adult male rat weighing 200–300 g is anesthetized with halothane in a mixture of $O_2$ and NO (1:2 ratio) and a midline incision is made in the ventral neck region. An indwelling venous catheter is placed in the jugular vein. The common carotid artery is exposed and dissected free from the vagus and cervical sympathetic nerves. One 4-0 silk suture ligature is tied securely. The animal is the placed in a restraint so that the right side of the head is facing up. The area is rubbed with betadiene and then the incision through the skin and the temporalis muscle is made in order to expose the skull. Care should be taken no to cut the large vein that is visible through the muscle. Once the skull is exposed the middle carotid artery is visible through the skull. Using a Foredom micro drill with a 4 mm burr bit, a small (approximately 8 mm) hole is made in the skull directly above the middle carotid artery. After drilling through the skull there is usually a thin layer of skull remaining that is carefully removed with fine forceps. Remove the dura, as required, away from the area directly above the middle carotid artery. The right middle cerebral artery occlusion is then performed by electrocoagulation without damaging the brain. The middle cerebral artery is cauterized immediately distal to the inferior cortical vein. A small piece of foam gel is then placed in the area and the muscle and skin in sutured with 3-0 silk. Compound or vehicle alone is administered intravenously at a predetermined time post-ischemia and dosing can be single, multiple, or by continuous infusion.

Animals are given food and water and allowed to survive for 24 h. The animal is then decapitated, the brain is removed, sliced into six sections and incubated in 2% 2,3,5-triphenyltetrazolium chloride for 30 minutes, as described by K. Isayama et al., *Evaluation of 2,3,5-Triphenyltetrazolium Chloride Stains to Delineate Rat Brain Infarcts, Stroke* 22, 1394–1398 (1991). The area of infarction is clearly visible. Infarct area is determined by computer-assisted image analysis for each of the six sections and integrated over the anterior-posterior extent of the brain to yield infarct volume. Group means±SE are determined for infarct volume and for the four behavioral tests and compared for the groups using ANOVA with orthogonal contrasts.

The compounds are also useful in the treatment of neurodegenerative diseases. It is understood that the term "neurodegeneration" refers to a progressive death and disappearance of a population of nerve cells occurring in a manner characteristic of a particular disease state and leading to brain damage. The term neurodegenerative diseases, includes Huntington's disease, Alzheimer's disease, senile dementia, glutaric acidaemia type I, multi-infarct dementia, amyotrophic lateral sclerosis, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, physical injury, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., *Distress Vocalization in Rat Pups: A Simple Screening Method For Anxiolytic Drugs, J. Pharmacol. Methods*, 14, 181–87 (1986) and Insel et.al., *Rat Pup Isolation Calls: Possible Mediation by the Benzodiazepine Receptor Complex, Pharmacol. Biochem. Behav.*, 24, 1263–67 (1986).

The compounds also exhibit an analgesic effect and are useful in controlling pain. The compounds are also effective in the treatment of migraine.

As excitatory amino acid antagonists, the compounds of formula (1) are useful in the treatment of excitatory amino acid-mediated diseases and conditions, including: neurodegenerative diseases, convulsive disorders, ischemic/hypoxic/hypoglycemic damage to cerebral tissue, anxiety, pain, migraine, and others known to those skilled in the art.

In a further embodiment, as excitatory amino acid antagonists, the present invention provides a method of treating excitatory amino acid-mediated diseases and conditions, including: neurodegenerative diseases, convulsive disorders, ischemic/hypoxic/hypoglycemic damage to cerebral tissue, anxiety, pain, and migraine in a patient in need thereof comprising administering to said patient a therapeutically effective amount of a compound of formula (1).

As used herein, the term "patient" refers to a warm blooded animal, such as a mammal, which is afflicted with a particular allergic disease. It is understood that guinea pigs, dogs, cats, rats, mice, horses, cattle, sheep, monkeys, chimpanzees, and humans are examples of animals within the scope of the meaning of the term.

As used herein, the term "therapeutically effective amount" of a compound of formula (1) refers to an amount which is effective in treating the diseases and conditions described herein. The term "treat" is intended to refer to all processes wherein there may be a slowing, interrupting, arresting, or stopping of the progression of the diseases and conditions described herein, but does not necessarily indicate a total elimination of all disease symptoms and is intended to include prophylactic treatment of the diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease or condition involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 50 mg/kg/day. Preferred amounts are able to be determined by one skilled in the art.

In effecting treatment of a patient afflicted with diseases and conditions described herein, a compound of formula (1) can be administered in any form or mode which makes the compound bioavailable in an effective amount, including oral and parenteral routes. For example, compounds of formula (1) can be administered orally, subcutaneously, intramuscularly, intravenously, transdermally, rectally, topically, and the like. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility, and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 80% of the weight thereof. The amount of the compound of formula (1) present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 20% w/v (weight per unit volume).

The compounds of the present invention may be administered topically by simply preparing a solution of the compound to be administered, preferably using a solvent known to promote transdermal absorption such as ethanol or dimethyl sulfoxide (DMSO) with or without other excipients.

Preferably topical administration will be accomplished using a patch either of the reservoir and porous membrane type or of a solid matrix variety. Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

Neurodegenerative diseases are typically associated with a loss of NMDA receptors. Thus, the compounds of formula (1) may be utilized in diagnostic procedures to aid physicians with the diagnosis of neurodegenerative diseases. The compounds may be labeled with imaging agents known in the art such as isotopic ions and administered to a patient in order to determine whether the patient is exhibiting a decreased number of NMDA receptors and the rate at which that loss is occurring.

What is claimed is:
1. A compound of the formula

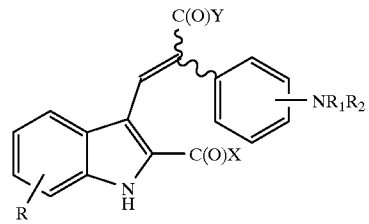

wherein
X is chosen from the group consisting of hydroxy, physiologically acceptable ester, and physiologically acceptable amide;
Y is chosen from the group consisting of hydroxy, physiologically acceptable ester, and physiologically acceptable amide;
R is from 1 to 3 substituents independently chosen from the group consisting of hydrogen, $C_1$–$C_4$ alkyl, $C_1$–$C_4$ alkoxy, halogen, —$CF_3$, and —$OCF_3$;
$R_1$ is chosen from the group consisting of hydrogen and $C_1$–$C_4$ alkyl;
$R_2$ is a radical chosen from the group consisting of

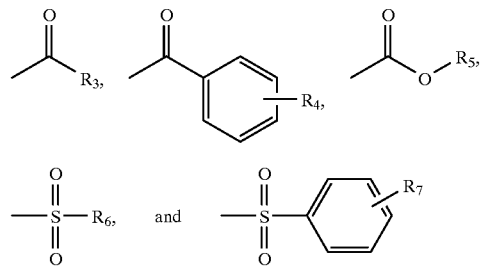

wherein
$R_3$ is chosen from the group consisting of hydrogen and $C_1$–$C_4$ alkyl;
$R_4$ is from 1 to 2 substituents independently chosen from the group consisting of hydrogen, $C_1$–$C_4$ alkyl, $C_1$–$C_4$ alkoxy, halogen, and —$CF_3$;
$R_5$ is $C_1$–$C_4$ alkyl;
$R_6$ is $C_1$–$C_4$ alkyl;
$R_7$ is from 1 to 2 substituents independently chosen from the group consisting of hydrogen, $C_1$–$C_4$ alkyl, $C_1$–$C_4$ alkoxy, halogen, and —$CF_3$;
and pharmaceutically acceptable addition salts thereof.
2. A compound of claim 1 wherein $R_2$ a radical chosen from the group consisting of

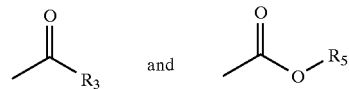

wherein
$R_3$ is chosen from the group consisting of hydrogen and $C_1$–$C_4$ alkyl; and
$R_5$ is $C_1$–$C_4$ alkyl.
3. A compound of claim 1 wherein X is chosen from the group consisting of hydroxy, $C_1$–$C_4$ alkoxy, and —$NH_2$.

4. A compound of claim 3 wherein X is chosen from the group consisting of hydroxy, methoxy, ethoxy and —NH$_2$.

5. A compound of claim 3 wherein X is hydroxy.

6. A compound of claim 1 wherein Y is chosen from the group consisting of hydroxy, C$_1$–C$_4$ alkoxy, and —NH$_2$.

7. A compound of claim 6 wherein Y is chosen from the group consisting of hydroxy, methoxy, ethoxy and —NH$_2$.

8. A compound of claim 6 wherein Y is hydroxy.

9. A compound of claim 1 wherein the compound is (E) or (Z)-2-(3-Acetamidophenyl)-3-(2-carboethoxy-4,6-dichloroindol-3-yl)-propenoic acid, methyl ester or a mixture thereof.

10. A compound of claim 1 wherein the compound is (E) or (Z)-2-(3-Benzamidophenyl)-3-(2-carboethoxy-4,6-dichloroindol-3-yl)-propenoic acid, methyl ester or a mixture thereof.

11. A compound of claim 1 wherein the compound is (E) or (Z)-2-(3-(N-Carbomethyloxyamino)phenyl)-3-(2-carboethoxy-4,6-dichloroindol-3-yl)-propenoic acid, methyl ester or a mixture thereof.

12. A compound of claim 1 wherein the compound is (E) or (Z)-2-(3-(N-Carboethyloxyamino)phenyl)-3-(2-carboethoxy-4,6-dichloroindol-3-yl)-propenoic acid, methyl ester or a mixture thereof.

13. A compound of claim 1 wherein the compound is (E) or (Z)-2-(3-(N-Carboisopropyloxyamino)phenyl)-3-(2-carboethoxy-4,6-dichloroindol-3-yl)-propenoic acid, methyl ester or a mixture thereof.

14. A compound of claim 1 wherein the compound is (E) or (Z)-2-(3-Methylsulfonylamidophenyl)-3-(2-carboethoxy-4,6-dichloroindol-3-yl)-propenoic acid, methyl ester or a mixture thereof.

15. A compound of claim 1 wherein the compound is (E)-2-(3-Acetamidophenyl)-3-(4,6-dichloroindol-3-yl-2-carboxylic acid)-propenoic acid.

16. A compound of claim 1 wherein the compound is (E)-2-(3-Benzamidophenyl)-3-(4,6-dichloroindol-3-yl-2-carboxylic acid)-propenoic acid.

17. A compound of claim 1 wherein the compound is (E)-2-(3-(N-Carbomethyloxyamino)phenyl)-3-(4,6-dichloroindol-3-yl-2-carboxylic acid)-propenoic acid.

18. A compound of claim 1 wherein the compound is (E)-2-(3-(N-Carboethyloxyamino)phenyl)-3-(4,6-dichloroindol-3-yl-2-carboxylic acid)-propenoic acid.

19. A compound of claim 1 wherein the compound is (E)-2-(3-(N-Carboisopropyloxyamino)phenyl)-3-(4,6-dichloroindol-3-yl-2-carboxylic acid)-propenoic acid.

20. A compound of claim 1 wherein the compound is (E)-2-(3-Methylsulfonylamidophenyl)-3-(4,6-dichloroindol-3-yl-2-carboxylic acid)-propenoic acid.

21. A compound of claim 1 wherein the compound is (Z)-2-(3-Acetamidophenyl)-3-(4,6-dichloroindol-3-yl-2-carboxylic acid)-propenoic acid.

22. A compound of claim 1 wherein the compound is (Z)-2-(3-Benzamidophenyl)-3-(4,6-dichloroindol-3-yl-2-carboxylic acid)-propenoic acid.

23. A compound of claim 1 wherein the compound is (Z)-2-(3-(N-Carbomethyloxyamino)phenyl)-3-(4,6-dichloroindol-3-yl-2-carboxylic acid)-propenoic acid.

24. A compound of claim 1 wherein the compound is (Z)-2-(3-(N-Carboethyloxyamino)phenyl)-3-(4,6-dichloroindol-3-yl-2-carboxylic acid)-propenoic acid.

25. A compound of claim 1 wherein the compound is (Z)-2-(3-(N-Carboisopropyloxyamino)phenyl)-3-(4,6-dichloroindol-3-yl-2-carboxylic acid)-propenoic acid.

26. A compound of claim 1 wherein the compound is (Z)-2-(3-Methylsulfonylamidophenyl)-3-(4,6-dichloroindol-3-yl-2-carboxylic acid)-propenoic acid.

27. A pharmaceutical composition comprising a therapeutically effective amount of a compound according to claim 1.

28. A pharmaceutical composition comprising a therapeutically effective amount of a compound according to claim 1 in admixture with a pharmaceutically accepted carrier.

29. A method for the treatment of neurodegenerative diseases comprising administering to a patient in need thereof a therapeutically effective amount of a compound according to claim 1.

30. A method for minimizing ischemic/hypoxic/hypoglycemic damage to cerebral tissue comprising administering to a patient in need thereof a therapeutically effective amount of a compound according to claim 1.

31. A method for the treatment of anxiety comprising administering a therapeutically effective amount of a compound according to claim 1.

32. A method for producing an analgesic effect comprising administering to a patient in need thereof a therapeutically effective amount of a compound according to claim 1.

* * * * *

UNITED STATES PATENT AND TRADEMARK OFFICE
CERTIFICATE OF CORRECTION

PATENT NO. : 5,922,752

DATED : July 13, 1999

INVENTOR(S) : Boyd L. Harrison, et al.

It is certified that error appears in the above-identified patent and that said Letters Patent is hereby corrected as shown below:

Column 1, line 5, after "1997" insert --and accorded the priority filing date of September 30, 1996--.

Signed and Sealed this

Eighth Day of February, 2000

Attest:

Q. TODD DICKINSON

*Attesting Officer*    *Commissioner of Patents and Trademarks*